(12) United States Patent
Ochs et al.

(10) Patent No.: US 8,275,553 B2
(45) Date of Patent: Sep. 25, 2012

(54) SYSTEM AND METHOD FOR EVALUATING PHYSIOLOGICAL PARAMETER DATA

(75) Inventors: James Ochs, Seattle, WA (US); Scott Amundson, Oakland, CA (US); Keith Batchelder, New York, NY (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 653 days.

(21) Appl. No.: 12/388,114

(22) Filed: Feb. 18, 2009

(65) Prior Publication Data

US 2009/0210163 A1    Aug. 20, 2009

Related U.S. Application Data

(60) Provisional application No. 61/066,181, filed on Feb. 19, 2008.

(51) Int. Cl.
*G01N 33/48* (2006.01)
(52) U.S. Cl. .................................................. 702/19
(58) Field of Classification Search .................. 702/19, 702/182–185, 188
See application file for complete search history.

(56) References Cited

U.S. PATENT DOCUMENTS

| | | |
|---|---|---|
| 3,638,640 A | 2/1972 | Shaw |
| 4,106,503 A | 8/1978 | Rosenthal et al. |
| 4,365,636 A | 12/1982 | Barker |
| 4,523,279 A | 6/1985 | Sperinde |
| 4,630,614 A | 12/1986 | Atlas |
| 4,651,746 A | 3/1987 | Wall |
| 4,714,341 A | 12/1987 | Hamaguri et al. |
| 4,738,266 A | 4/1988 | Thatcher |
| 4,757,824 A | 7/1988 | Chaumet |
| 4,765,340 A | 8/1988 | Sakai et al. |
| 4,802,485 A | 2/1989 | Bowers et al. |
| 4,805,623 A | 2/1989 | Jöbsis |
| 4,807,631 A | 2/1989 | Hersh et al. |
| 4,869,253 A | 9/1989 | Craig |

(Continued)

FOREIGN PATENT DOCUMENTS

DE    9 200 422.9    7/1992

(Continued)

OTHER PUBLICATIONS

Aboyans, V., et al., Sleep Apnoea Syndrome and the Extent of Atherosclerotic Lesions in Middle/Aged Men with Myocardial Infarction, International Angiology, Mar. 1999, vol. 18, No. 1, pp. 70-73.

(Continued)

*Primary Examiner* — Edward Raymond
(74) *Attorney, Agent, or Firm* — Fletcher Yoder

(57) ABSTRACT

Embodiments disclosed herein may include systems and methods for evaluating physiological parameter data. Embodiments of methods may include monitoring a patient to produce a signal comprising a sequence of numerical values for a physiological parameter over a time period, calculating an index from the signal, comparing the index to a reported index, and if the index is greater than the reported index, setting the reported index to the value of the index. Embodiments of methods may include calculating a modulation of the signal, comparing the modulation to a previous value of the modulation to identify a trend in the modulation and if the trend corresponds to an undesirable condition, using a first function to increase the reported index. Embodiments of methods may include providing an indication of a physiological status based on the reported index.

17 Claims, 8 Drawing Sheets

U.S. PATENT DOCUMENTS

| | | |
|---|---|---|
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,111,817 A | 5/1992 | Clark et al. |
| 5,119,815 A | 6/1992 | Chance |
| 5,122,974 A | 6/1992 | Chance |
| 5,123,420 A | 6/1992 | Paret |
| 5,134,995 A | 8/1992 | Gruenke et al. |
| 5,167,230 A | 12/1992 | Chance |
| 5,190,038 A | 3/1993 | Polson et al. |
| 5,199,424 A | 4/1993 | Sullivan |
| 5,206,807 A | 4/1993 | Hatke |
| 5,218,962 A | 6/1993 | Mannheimer et al. |
| 5,233,983 A | 8/1993 | Markowitz |
| 5,246,003 A | 9/1993 | DeLonzor |
| 5,247,931 A | 9/1993 | Norwood |
| 5,263,244 A | 11/1993 | Centa et al. |
| 5,275,159 A | 1/1994 | Griebel |
| 5,279,295 A | 1/1994 | Martens et al. |
| 5,297,548 A | 3/1994 | Pologe |
| 5,303,699 A | 4/1994 | Bonassa et al. |
| 5,318,597 A | 6/1994 | Hauck et al. |
| 5,329,931 A | 7/1994 | Clauson et al. |
| 5,335,654 A | 8/1994 | Rapoport |
| 5,353,788 A | 10/1994 | Miles |
| 5,355,880 A | 10/1994 | Thomas et al. |
| 5,368,026 A | 11/1994 | Swedlow et al. |
| 5,372,136 A | 12/1994 | Steuer et al. |
| 5,385,143 A | 1/1995 | Aoyagi |
| 5,385,144 A | 1/1995 | Yamanishi et al. |
| 5,390,670 A | 2/1995 | Centa et al. |
| 5,398,682 A | 3/1995 | Lynn |
| 5,413,099 A | 5/1995 | Schmidt et al. |
| 5,469,845 A | 11/1995 | DeLonzor et al. |
| 5,482,036 A | 1/1996 | Diab et al. |
| 5,483,646 A | 1/1996 | Uchikoga |
| 5,483,969 A | 1/1996 | Testerman |
| 5,485,851 A | 1/1996 | Erickson |
| 5,490,502 A | 2/1996 | Rapoport et al. |
| 5,535,739 A | 7/1996 | Rapoport et al. |
| 5,540,733 A | 7/1996 | Testerman et al. |
| 5,549,106 A | 8/1996 | Gruenke et al. |
| 5,551,419 A | 9/1996 | Froehlich et al. |
| 5,553,614 A | 9/1996 | Chance |
| 5,564,417 A | 10/1996 | Chance |
| 5,575,285 A | 11/1996 | Takanashi et al. |
| 5,605,151 A | 2/1997 | Lynn |
| 5,611,337 A | 3/1997 | Bukta |
| 5,630,413 A | 5/1997 | Thomas et al. |
| 5,632,270 A | 5/1997 | O'Mahony et al. |
| 5,645,053 A | 7/1997 | Remmers et al. |
| 5,645,054 A | 7/1997 | Cotner et al. |
| 5,645,059 A | 7/1997 | Fein et al. |
| 5,645,060 A | 7/1997 | Yorkey |
| 5,680,857 A | 10/1997 | Pelikan et al. |
| 5,682,878 A | 11/1997 | Ogden |
| 5,692,503 A | 12/1997 | Keunstner |
| 5,704,345 A | 1/1998 | Berthon/Jones |
| 5,730,124 A | 3/1998 | Yamauchi |
| 5,730,144 A | 3/1998 | Katz et al. |
| 5,740,795 A | 4/1998 | Brydon |
| 5,743,250 A | 4/1998 | Gonda et al. |
| 5,749,900 A | 5/1998 | Schroeppel et al. |
| 5,751,911 A | 5/1998 | Goldman |
| 5,758,644 A | 6/1998 | Diab et al. |
| 5,765,563 A | 6/1998 | Vander Schaaf |
| 5,769,084 A | 6/1998 | Katz et al. |
| 5,779,631 A | 7/1998 | Chance |
| 5,782,240 A | 7/1998 | Raviv et al. |
| 5,782,757 A | 7/1998 | Diab et al. |
| 5,786,592 A | 7/1998 | Hök |
| 5,794,614 A | 8/1998 | Gruenke et al. |
| 5,794,615 A | 8/1998 | Estes |
| 5,803,065 A | 9/1998 | Zdrojkowski et al. |
| 5,803,066 A | 9/1998 | Rapoport et al. |
| 5,823,187 A | 10/1998 | Estes et al. |
| 5,827,179 A | 10/1998 | Lichter et al. |
| 5,830,135 A | 11/1998 | Bosque et al. |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,845,636 A | 12/1998 | Gruenke et al. |
| 5,853,364 A | 12/1998 | Baker et al. |
| 5,865,173 A | 2/1999 | Froehlich |
| 5,865,736 A | 2/1999 | Baker, Jr. et al. |
| 5,871,442 A | 2/1999 | Madarasz et al. |
| 5,873,821 A | 2/1999 | Chance et al. |
| 5,891,022 A | 4/1999 | Pologe |
| 5,891,023 A | 4/1999 | Lynn |
| 5,902,250 A | 5/1999 | Verrier et al. |
| 5,920,263 A | 7/1999 | Huttenhoff et al. |
| 5,957,885 A | 9/1999 | Bollish |
| 5,995,855 A | 11/1999 | Kiani et al. |
| 5,995,856 A | 11/1999 | Mannheimer et al. |
| 5,995,859 A | 11/1999 | Takahashi |
| 6,006,379 A | 12/1999 | Hensley |
| 6,011,986 A | 1/2000 | Diab et al. |
| 6,015,388 A | 1/2000 | Sackner et al. |
| 6,064,898 A | 5/2000 | Aldrich |
| 6,081,742 A | 6/2000 | Amano et al. |
| 6,083,156 A | 7/2000 | Lisiecki |
| 6,088,607 A | 7/2000 | Diab et al. |
| 6,105,575 A | 8/2000 | Estes et al. |
| 6,120,441 A | 9/2000 | Griebel |
| 6,120,460 A | 9/2000 | Abreu |
| 6,134,460 A | 10/2000 | Chance |
| 6,138,675 A | 10/2000 | Berthon/Jones |
| 6,144,877 A | 11/2000 | DePetrillo |
| 6,148,814 A | 11/2000 | Clemmer et al. |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,190,324 B1 | 2/2001 | Kieval et al. |
| 6,215,403 B1 | 4/2001 | Chan et al. |
| 6,216,032 B1 | 4/2001 | Griffin et al. |
| 6,223,064 B1 | 4/2001 | Lynn et al. |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,286,508 B1 | 9/2001 | Remmers et al. |
| 6,299,581 B1 | 10/2001 | Rapoport et al. |
| 6,305,374 B1 | 10/2001 | Zdrojkowski et al. |
| 6,312,393 B1 | 11/2001 | Abreu |
| 6,322,515 B1 | 11/2001 | Goor et al. |
| 6,342,039 B1 | 1/2002 | Lynn et al. |
| 6,345,619 B1 | 2/2002 | Finn |
| 6,353,750 B1 | 3/2002 | Kimura et al. |
| 6,360,114 B1 | 3/2002 | Diab et al. |
| 6,367,474 B1 | 4/2002 | Berthon/Jones et al. |
| 6,371,113 B1 | 4/2002 | Tobia et al. |
| 6,375,623 B1 | 4/2002 | Gavriely |
| 6,397,091 B2 | 5/2002 | Diab et al. |
| 6,397,092 B1 | 5/2002 | Norris et al. |
| 6,401,713 B1 | 6/2002 | Hill et al. |
| 6,415,236 B2 | 7/2002 | Kobayashi et al. |
| 6,419,671 B1 | 7/2002 | Lemberg |
| 6,425,861 B1 | 7/2002 | Haberland et al. |
| 6,438,399 B1 | 8/2002 | Kurth |
| 6,449,501 B1 | 9/2002 | Reuss |
| 6,461,305 B1 | 10/2002 | Schnall |
| 6,463,326 B1 | 10/2002 | Hartley et al. |
| 6,466,809 B1 | 10/2002 | Riley |
| 6,487,439 B1 | 11/2002 | Skladnev et al. |
| 6,488,634 B1 | 12/2002 | Rapoport et al. |
| 6,501,974 B2 | 12/2002 | Huiku |
| 6,501,975 B2 | 12/2002 | Diab et al. |
| 6,502,572 B1 | 1/2003 | Berthon/Jones et al. |

| Patent No. | Date | Inventor(s) |
|---|---|---|
| 6,519,486 B1 | 2/2003 | Edgar, Jr. et al. |
| 6,526,301 B2 | 2/2003 | Larsen et al. |
| 6,529,752 B2 | 3/2003 | Krausman et al. |
| 6,532,960 B1 | 3/2003 | Yurko |
| 6,539,940 B2 | 4/2003 | Zdrojkowski et al. |
| 6,542,764 B1 | 4/2003 | Al/Ali et al. |
| 6,544,193 B2 | 4/2003 | Abreu |
| 6,546,267 B1 | 4/2003 | Sugiura et al. |
| 6,549,795 B1 | 4/2003 | Chance |
| 6,572,557 B2 | 6/2003 | Tchou et al. |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,609,016 B1 | 8/2003 | Lynn |
| 6,609,517 B1 | 8/2003 | Estes et al. |
| 6,615,064 B1 | 9/2003 | Aldrich |
| 6,618,042 B1 | 9/2003 | Powell |
| 6,622,095 B2 | 9/2003 | Kobayashi et al. |
| 6,622,726 B1 | 9/2003 | Du |
| 6,637,434 B2 | 10/2003 | Noble |
| 6,640,806 B2 | 11/2003 | Yurko |
| 6,641,542 B2 | 11/2003 | Cho et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,661,161 B1 | 12/2003 | Lanzo et al. |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,675,797 B1 | 1/2004 | Berthon/Jones |
| 6,678,543 B2 | 1/2004 | Diab et al. |
| 6,684,090 B2 | 1/2004 | Ali et al. |
| 6,690,958 B1 | 2/2004 | Walker et al. |
| 6,691,705 B2 | 2/2004 | Dittman et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,719,705 B2 | 4/2004 | Mills |
| 6,731,274 B2 | 5/2004 | Powell |
| 6,745,764 B2 | 6/2004 | Hickle |
| 6,748,252 B2 | 6/2004 | Lynn |
| 6,760,608 B2 | 7/2004 | Lynn |
| 6,761,167 B1 | 7/2004 | Nadjafizadeh et al. |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,804,656 B1 | 10/2004 | Rosenfeld et al. |
| 6,807,965 B1 | 10/2004 | Hickle |
| 6,814,074 B1 | 11/2004 | Nadjafizadeh et al. |
| 6,817,361 B2 | 11/2004 | Berthon/Jones et al. |
| 6,822,564 B2 | 11/2004 | Al/Ali |
| 6,829,496 B2 | 12/2004 | Nagai et al. |
| 6,832,200 B2 | 12/2004 | Greeven et al. |
| 6,839,581 B1 | 1/2005 | El-Solh et al. |
| 6,850,053 B2 | 2/2005 | Daalmans et al. |
| 6,863,652 B2 | 3/2005 | Huang et al. |
| 6,873,865 B2 | 3/2005 | Steuer et al. |
| 6,889,153 B2 | 5/2005 | Dietiker |
| 6,896,660 B2 | 5/2005 | Jelliffe et al. |
| 6,898,451 B2 | 5/2005 | Wuori |
| 6,932,084 B2 | 8/2005 | Estes et al. |
| 6,939,307 B1 | 9/2005 | Dunlop |
| 6,947,780 B2 | 9/2005 | Scharf |
| 6,948,497 B2 | 9/2005 | Zdrojkowski et al. |
| 6,949,081 B1 | 9/2005 | Chance |
| 6,961,598 B2 | 11/2005 | Diab |
| 6,983,178 B2 | 1/2006 | Fine et al. |
| 6,988,498 B2 | 1/2006 | Berthon-Jones |
| 6,993,371 B2 | 1/2006 | Kiani et al. |
| 6,996,427 B2 | 2/2006 | Ali et al. |
| 7,006,676 B1 | 2/2006 | Zeylikovich et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,031,857 B2 | 4/2006 | Tarassenko et al. |
| 7,035,697 B1 | 4/2006 | Brown |
| 7,047,056 B2 | 5/2006 | Hannula et al. |
| 7,081,095 B2 | 7/2006 | Lynn et al. |
| 7,090,648 B2 | 8/2006 | Sackner et al. |
| 7,123,950 B2 | 10/2006 | Mannheimer |
| 7,127,278 B2 | 10/2006 | Melker et al. |
| 7,153,263 B2 | 12/2006 | Carter et al. |
| 7,162,306 B2 | 1/2007 | Caby et al. |
| 7,209,775 B2 | 4/2007 | Bae et al. |
| 7,225,013 B2 | 5/2007 | Geva et al. |
| 7,236,811 B2 | 6/2007 | Schmitt |
| 7,246,620 B2 | 7/2007 | Conroy, Jr. |
| 7,247,154 B2 | 7/2007 | Hickle |
| 7,263,395 B2 | 8/2007 | Chan et al. |
| 7,272,426 B2 | 9/2007 | Schmid |
| 7,297,119 B2 | 11/2007 | Westbrook et al. |
| 7,309,314 B2 | 12/2007 | Grant et al. |
| 7,338,447 B2 | 3/2008 | Phillips |
| 7,349,727 B2 | 3/2008 | Obata et al. |
| 7,366,569 B2 | 4/2008 | Belalcazar |
| 7,373,193 B2 | 5/2008 | Al-Ali et al. |
| 7,383,105 B2 | 6/2008 | Conroy, Jr. |
| 7,398,115 B2 | 7/2008 | Lynn |
| 7,407,486 B2 | 8/2008 | Huiku et al. |
| 7,438,687 B2 | 10/2008 | Lewicke |
| 7,460,909 B1 | 12/2008 | Koh et al. |
| 7,539,533 B2 * | 5/2009 | Tran ............................ 600/509 |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0117173 A1 | 8/2002 | Lynn et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0158466 A1 | 8/2003 | Lynn |
| 2003/0220548 A1 | 11/2003 | Schmitt |
| 2003/0220576 A1 | 11/2003 | Diab |
| 2004/0010188 A1 | 1/2004 | Wasserman |
| 2004/0015091 A1 | 1/2004 | Greenwald et al. |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0111014 A1 | 6/2004 | Hickle |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0016536 A1 | 1/2005 | Rapoport et al. |
| 2005/0043763 A1 | 2/2005 | Marcovecchio et al. |
| 2005/0080323 A1 | 4/2005 | Kato |
| 2005/0081854 A1 | 4/2005 | Nadjafizadeh et al. |
| 2005/0101850 A1 | 5/2005 | Parker |
| 2005/0113651 A1 | 5/2005 | Wood et al. |
| 2005/0113656 A1 | 5/2005 | Chance |
| 2005/0113709 A1 | 5/2005 | Millet |
| 2005/0119586 A1 | 6/2005 | Coyle et al. |
| 2005/0143665 A1 | 6/2005 | Huiku et al. |
| 2005/0168722 A1 | 8/2005 | Forstner et al. |

| | | | |
|---|---|---|---|
| 2005/0177034 A1 | 8/2005 | Beaumont | |
| 2005/0187480 A1 | 8/2005 | Kario et al. | |
| 2005/0192488 A1 | 9/2005 | Bryenton et al. | |
| 2005/0203357 A1 | 9/2005 | Debreczeny et al. | |
| 2005/0228248 A1 | 10/2005 | Dietiker | |
| 2005/0267346 A1 | 12/2005 | Faber et al. | |
| 2005/0283059 A1 | 12/2005 | Iyer et al. | |
| 2006/0009688 A1 | 1/2006 | Lamego et al. | |
| 2006/0009809 A1 | 1/2006 | Marcovecchio et al. | |
| 2006/0015021 A1 | 1/2006 | Cheng | |
| 2006/0020181 A1 | 1/2006 | Schmitt | |
| 2006/0030763 A1 | 2/2006 | Mannheimer et al. | |
| 2006/0052680 A1 | 3/2006 | Diab | |
| 2006/0058683 A1 | 3/2006 | Chance | |
| 2006/0064024 A1 | 3/2006 | Schnall | |
| 2006/0137577 A1 | 6/2006 | Chang et al. | |
| 2006/0155207 A1 | 7/2006 | Lynn et al. | |
| 2006/0161071 A1 | 7/2006 | Lynn et al. | |
| 2006/0167362 A1 | 7/2006 | Neumann et al. | |
| 2006/0173257 A1 | 8/2006 | Nagai et al. | |
| 2006/0189880 A1 | 8/2006 | Lynn et al. | |
| 2006/0195028 A1 | 8/2006 | Hannula et al. | |
| 2006/0195041 A1 | 8/2006 | Lynn et al. | |
| 2006/0217615 A1 | 9/2006 | Huiku et al. | |
| 2006/0224058 A1 | 10/2006 | Mannheimer | |
| 2006/0225737 A1 | 10/2006 | Iobbi | |
| 2006/0235324 A1 | 10/2006 | Lynn | |
| 2006/0247501 A1 | 11/2006 | Ali | |
| 2006/0258921 A1 | 11/2006 | Addison et al. | |
| 2006/0276695 A9 | 12/2006 | Lynn et al. | |
| 2007/0027375 A1 | 2/2007 | Melker et al. | |
| 2007/0066910 A1 | 3/2007 | Inukai et al. | |
| 2007/0093721 A1 | 4/2007 | Lynn et al. | |
| 2007/0119453 A1 | 5/2007 | Lu et al. | |
| 2007/0123785 A1 | 5/2007 | Lu et al. | |
| 2007/0149860 A1 | 6/2007 | Lynn et al. | |
| 2007/0203406 A1 | 8/2007 | Anderson et al. | |
| 2007/0208269 A1 | 9/2007 | Mumford et al. | |
| 2007/0213619 A1 | 9/2007 | Linder | |
| 2007/0213620 A1 | 9/2007 | Reisfeld | |
| 2007/0213621 A1 | 9/2007 | Reisfeld et al. | |
| 2007/0213622 A1 | 9/2007 | Reisfeld | |
| 2007/0213624 A1 | 9/2007 | Reisfeld et al. | |
| 2007/0238937 A1 | 10/2007 | Chang et al. | |
| 2007/0240723 A1 | 10/2007 | Hong et al. | |
| 2007/0276262 A1 | 11/2007 | Banet et al. | |
| 2008/0009689 A1 | 1/2008 | Benaron et al. | |
| 2008/0064965 A1 | 3/2008 | Jay et al. | |
| 2008/0071155 A1 | 3/2008 | Kiani | |
| 2008/0082018 A1 | 4/2008 | Sackner et al. | |
| 2008/0091088 A1 | 4/2008 | Kiani | |
| 2008/0139908 A1 | 6/2008 | Kurth | |
| 2008/0177163 A1 | 7/2008 | Wang et al. | |
| 2008/0177358 A1 | 7/2008 | Gammons | |
| 2008/0188729 A1 | 8/2008 | Sato et al. | |
| 2008/0200775 A1 | 8/2008 | Lynn | |
| 2008/0221464 A1 | 9/2008 | Al-Ali | |
| 2008/0262362 A1 | 10/2008 | Kolluri et al. | |
| 2008/0275317 A1 | 11/2008 | Cho et al. | |
| 2008/0287756 A1 | 11/2008 | Lynn | |
| 2008/0312533 A1 | 12/2008 | Balberg et al. | |
| 2008/0314385 A1 | 12/2008 | Brunner et al. | |

FOREIGN PATENT DOCUMENTS

| | | |
|---|---|---|
| EP | 0615723 | 3/1993 |
| EP | 0459284 B1 | 1/1995 |
| EP | 0651971 A1 | 10/1995 |
| EP | 0709107 A1 | 5/1996 |
| EP | 0714670 A2 | 6/1996 |
| EP | 0722747 A2 | 7/1996 |
| EP | 0788805 A3 | 5/1998 |
| EP | 0968734 A3 | 1/2000 |
| EP | 1004325 A3 | 6/2000 |
| EP | 0700690 B1 | 2/2002 |
| EP | 0759791 B1 | 8/2002 |
| EP | 0934723 B1 | 9/2004 |
| EP | 1172123 B1 | 10/2004 |
| EP | 0875258 B1 | 11/2004 |
| EP | 1488743 A2 | 12/2004 |
| EP | 1790283 | 5/2007 |
| JP | 63275325 | 11/1988 |
| JP | 2005034472 | 2/2005 |
| WO | WO 88/01149 | 2/1988 |
| WO | WO 90/09146 | 8/1990 |
| WO | WO 90/14121 | 11/1990 |
| WO | WO9111137 A1 | 8/1991 |
| WO | WO 92/11054 | 7/1992 |
| WO | WO 92/22244 | 12/1992 |
| WO | WO9313706 A2 | 7/1993 |
| WO | WO93/16629 | 9/1993 |
| WO | WO 94/06499 | 3/1994 |
| WO | WO 94/23780 | 10/1994 |
| WO | WO 95/32016 | 11/1995 |
| WO | WO9639927 | 12/1996 |
| WO | WO 97/14462 | 4/1997 |
| WO | WO 97/28838 | 8/1997 |
| WO | WO9851212 A1 | 11/1998 |
| WO | WO 99/24099 | 5/1999 |
| WO | WO 99/45989 | 9/1999 |
| WO | WO0021438 | 4/2000 |
| WO | WO 00/67827 | 11/2000 |
| WO | WO0117421 | 3/2001 |
| WO | WO0140776 | 6/2001 |
| WO | WO0176461 | 10/2001 |
| WO | WO0176471 | 10/2001 |
| WO | WO03039326 | 5/2003 |
| WO | WO03084396 | 10/2003 |
| WO | WO 2004/047621 A2 | 6/2004 |
| WO | WO2004105601 | 12/2004 |
| WO | WO 2005/065757 A1 | 7/2005 |
| WO | WO2006092624 A1 | 9/2006 |
| WO | WO2007051066 | 5/2007 |
| WO | WO2008097411 A1 | 8/2008 |

OTHER PUBLICATIONS

Abraham, Howard et al., Sequential Cardiorespiratory Patterns in Septic Shock, Critical Care Medicine, vol. 11, No. 10, Oct. 1983, pp. 799-803.
Agilent Technologies, Agilent M1165/66/67/75/76/77A Component Monitoring System and Agilent M1205A V24 & V26, User's Reference Manual, vol. 1, System Information, Part No. M1046/9101L, First Ed., Printed Nov. 2000.
Agilent Technologies, Agilent M1165/66/67/75/76/77A Component Monitoring System and Agilent M1205A V24 & V26, User's Reference Manual, vol. 2, Parameter Information, Part No. M1046/9101L, First Ed., Printed Nov. 2000.
Aittokallio, Tero, et al., Analysis of Inspiratory Flow Shapes in Patients with Partial Upper/Airway Obstruction During Sleep, Chest, vol. 119, No. 1, Jan. 2001, pp. 37-44, Northbrook, IL, USA.
Alaris System, Brochure, Medication Safety System Focused at the Point of Care, Cardinal Health, Alaris Products, pp. 8, 2007.
Alchanatis, M., et al., Left ventricular function in patients with obstructive sleep apnoea syndrome before and after treatment with nasal continuous positive airway pressure, Respiration, 2000, vol. 67, No. 4, p. 367(Abstract).
Andreas, Stefan, et al., Prevalence of Obstructive Sleep Apnoea in Patients with Coronary Artery Disease, Coronary Artery Disease, Jul. 1996, vol. 7, No. 7, pp. 541-545.
Attin, M. et al.; *An Educational Project to Improve Knowledge Related to Pulse Oximetry*; American Journal of Critical Care, Nov. 2002, vol. 11, No. 6; pp. 529-534; US.
Aubry, et al., The $SaO_2$/t Diagram as a Useful Means to Express Nocturnal Hypoxemia, Chest, 1989; 96: 1341-45.
Author Unknown, 1998 New Survey Reports More Than 168 Million American Adults Fail Sleep IQ Test, 132 Million Suffer Sleep Problems, Feb. 1998, Life Magazine.
Author Unknown, Background of Oximetry Utilization for Sleep Apnea Diagnosis, Publication information unknown, Undated.
Author Unknown, Chapter IV Oxygen Consumption During ADO, Introduction, pp. 40-46, Book Title Unknown, Date Unknown.
Author Unknown, Chapter X Effects of a 6/minute Period of ADO, Introduction, pp. 108-113, Book Title Unknown, Date Unknown.
Author Unknown, Guidance Article, (No Author), Critical Alarms and Patient Safety, Health Devices, vol. 31, No. 11, Nov. 2002, pp. 397-417, 2002 ECRI.

Author Unknown, Excessive Daytime Sleepiness, News Bulletin, http://www.websciences.org/nsf/pressarchives/leadpressrelease_g.html, Jun. 3, 1997, Washington, DC, USA.
Author Unknown, News Bulletin, Lack of sleep America's top health problem, doctors say, Health Story Page, CNN, http://cnn.com/HEALTH/9703/17/nfm/sleep.deprivation/index.html, Mar. 17, 1997.
Author Unknown, Sleep Apnea & Heart Problems, News Channel WTVC, Chattanooga, Tennessee, USA, Jun. 3, 1999, News Bulletin.
Author Unknown, The Physiologic Parameters Defining the Oximetry Waveform Patterns in Sleep Apnea, Undated, Publication Unknown.
Author Unknown, The Ventilation Instability Detection Trial, Hospital Protocol, Early Discussion Draft, 4 pages, Facsimile dated Jul. 23, 2003, From SDC.
Ayas, Najib, et al., Unrecognized Severe Postoperative Hypercapnia: A Case of Apneic Oxygenation, Case Report, Mayo Clinic Proceedings, 1998, vol. 73, pp. 51-54, Minneapolis, Minnesota, USA.
Badoual, T., et al., Sleep Apnoea Syndrome and Cardiac Failure, Arch Mal Coeur Vaiss., Mar. 2005, vol. 98, No. 3, pp. 198-2, [Article in French] (Abstract).
BaHammam, A., Comparison of nasal prong pressure and thermistor measurements for detecting respiratory events during sleep, Respiration, Jul./Aug. 2004, vol. 71, No. 4, pp. 385-390 (Abstract).
Baker, Clark R., et al., Nellcor 04 Algorithm Summary, Copyright 1999 Mallinckrodt Inc., pp. 1-8.
Ball, Eric M., et al., Diagnosis and Treatment of Sleep Apnea Within the Community, The Walla Walla Project, Arch Intern Med, vol. 157, Feb. 24, 1997, pp. 419-424.
Barach, Alvan L., et al., The Physiologic Action of Oxygen and Carbon Dioxide on the Coronary Circulation, as Shown by Blood Gas and Electrocardiographic Studies, The American Heart Journal, Received for publication Aug. 14, 1940, pp. 13-38.
Barker, Steven J., The Effects of Motion on the Performance of Pulse Oximeters in Volunteers (Revised Publication), Anesthesiology, Lippincott/Raven Publishers, American Society of Anesthesiologists, Inc.(Revised Publication) 1997, vol. 86, pp. 101-108 (Both paper and Abstract).
Barnum, P. T., et al., Novel Pulse Oximetry Technology Capable of Reliable Bradycardia Monitoring in the Neonate, Respiratory Care, 1997, vol. 42, No. 11, pp. 1072 (Abstract).
Bartolo, Anton, et al., An Arrhythmia Detector and Heart Rate Estimator for Overnight Polysomnography Studies, conditionally accepted for Transactions, 19 pages, May 2001.
Bassetti, Claudio L., Sleep and Stroke, Seminars in Neurology, vol. 25, No. 1, Nov. 1, 2005, pp. 19-32.
Benumof, Jonathan L., Creation of Observational Unit May Decrease Sleep Apnea Risk, Letters to the Editor, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp, 2002.
Berg, Sören, et al., Continuous Intrathoracic Pressure Monitoring with a New Esophageal Microchip Catheter in Sleep/Related Upper Airway Obstructions, The Journal of Otolaryngology, vol. 24, No. 3, 1993, pp. 160-164.
Bernet/Buettiker, Vera et al., Evaluation of New Combined Transcutaneous Measurement of PCO2/Pulse Oximetry Oxygen Saturation Ear Sensor in Newborn Patients, Dec. 15, 2004, DOI: I0.1542/peds.2004/0946, Pediatrics Official Journal of the American Academy of Pediatrics, published online, pp. e/64-e68, Elk Grove Village, IL 60007, USA.
Berry, Richard B., Positive Nasal Airway Pressure Eliminates Snoring as Well as Obstructive Sleep Apnea, Chest, vol. 85, No. 1, Jan. 1984, pp. 15-20.
Berry, Richard B., et al., Comparison of Respiratory Event Detection by a Polyvinylidene Fluoride Film Airflow Sensor and a Pneumotachograph in Sleep Apnea Patients, Chest, The Cardiopulmonary and Critical Care Journal, Chest/128/3/Sep. 2005, pp. 1331-1338, Northbrook, IL, USA, 2005.

Berthon/Jones, M., et al., Time Course of Change in Ventilatory Response to $CO_2$ with Long/Term CPAP Therapy for Obstructive Sleep Apnea, American Review Respiratory Disease, 1987, vol. 135, pp. 144-147.
Berthon/Jones, Michael, Feasibility of a Self/Setting CPAP Machine, Sleep, vol. 16, pp. S120-S123, 1993.
Bixler, E. O., et al., Effects of age on sleep apnea in men: I. Prevalence and Severity, American Journal of Repiratory & Clinical Care Medicine, vol. 157, No. 1, pp. 144-148, Jan. 1998 (Abstract).
Blackshear et al., Nocturnal Dyspnea and Atrial Fibrillation Preset Cheyne—Stokes Respirations in Patients With Congestive Heart Failure, Jun. 26, 1995, Arch Intern Med. vol. 155, p. 1296-1302.
Blankfield, R. P., et al., Bilateral leg edema, obesity, pulmonary hypertension, and obstructive sleep apnea, Arch Intern Med., Aug. 14, 2000, vol. 28, 160(15), pp. 2357-62 (Abstract).
Blankfield, R. P., et al., Bilateral leg edema, pulmonary hypertension, and obstructive sleep apnea: a cross/sectional study, Family Practice, Jun. 2002, vol. 51, No. 6, pp. 561-564 (Abstract).
Block, A. Jay, et al., Sleep Apnea, Hypopnea and Oxygen Desaturation in Normal Subjects, A Strong Male Predominance, The New England Journal of Medicine, vol. 300, Mar. 8, 1979, pp. 513-517.
Blumen, M., et al., Dilator muscles of the pharynx and their implication in the sleep apnea syndrome of obstructive type. Review of the literature., [Article in French], Ann Otolaryngol Chir Cervicofac, May 1998, p. 115 (Abstract).
Bock, A. V. et al., The Oxygen and Carbon Dioxide Dissociation Curves of Human Blood (This is study No. 37 of a series of studies on the physiology and pathology of blood form the Harvard Medical School and allied Hospitals, a part of the expense of which has been defrayed by the Proctor Fund for the study of chronic disease, Journal of Biologic Chemistry, vol. 29, 1924, pp. 353-377.
Bohnhorst, B., et al., Major Reduction in Alarm Frequency With a New Pulse Oximeter, Intensive Care Medicine, 1998, vol. 24, No. 3, pp. 277-278 (Abstract).
Bordier, P., et al., Death during polysomnography of a patient with cheyne/stokes respiration, repiratory acidosis, and chronic heart failure, Chest, Nov. 2004, vol. 126, No. 5, pp. 1698-1700 (Abstract).
Botelho, Ricardo Vieira, et al., Adult Chiari Malformation and Sleep Apnoea, Published online May 21, 2005, Neurosurgeon Review, vol. 28, pp. 169-176, 2005.
Boushra, N. N., Anaesthetic management of patients with sleep apnoea syndrome, Canadian Journal Anaesth, Jun. 1996, vol. 45, No. 6, pp. 599-616 (Abstract).
Bowton, David L., et al., The Incidence and Effect on Outcome of Hypoxemia in Hospitalized Medical Patients, The American Journal of Medicine, Vo. 97, Jul. 1994, pp. 38-46.
Bradley, Douglas T., et al., Daytime Hypercapnia in the Developement of Nocturnal Hypoxemia in COPD, Chest, vol. 97, No. 2, Feb. 1990, pp. 308-312.
Brooks, L. J., et al., Adenoid size is related to severity but not the number of episodes of obstructive apnea in children, Journal of Pediatrics, vol. 132, No. 4, pp. 682-686, Apr. 1998 (Abstract).
Broughton, Roger J., et al., Practice Parameters for the Use of Stimulants in the Treatment of Narcolepsy, ASDA Standards of Practice, Sleep, vol. 17, No. 4, pp. 348-351, American Sleep Disorders Association and Sleep Research Society 1994.
Brown, Lee K., "Dephlogisticated air" revisited: oxygen treatment for central sleep apnea, 1997 American College of Chest Physician, Physician Information, No. 8, Rev. 01, Nov. 1997.
Brown, D. L., et al., Screening for obstructive sleep apnea in stroke patients: a cost/effectiveness analysis, Stroke, Jun. 2005, pp. 1291-1293, Epub May 12, 2005 (Abstract).
Buckle, Patricia, et al., Polysomnography in Acutely Ill Intensive Care Unit Patients, Chest, v. 102 n.1, p. 288 (4), American College of Chest Physicians, 1995.
Burk, John R., et al., Auto/CPAP in the Treatment of Obstructive Sleep Apnea: A New Approach Sleep Research 21, 1992, p. 182, Abstract.
Cain, S. M., Breaking Point of Two Breath Holds Separated by a Single Inspiration, Journal of Appl. Physiol., vol. II(I), Jul. 1957, pp. 87-90.
Campos/Rodriguez, Francisco, et al., Mortality in Obstructive Sleep Apnea/Hypopnea Patients Treated With Positive airway Pressure, Chest, The Cardiopulmonary and Critical Care Journal, 2005, vol. 128, pp. 624-633, Northbrook, Illinois, USA (plus Abstract).
Cannesson, Maxime et al., Relation between respiratory variations in pulse oximetry plethsmographic waveform amplitude and arterial pulse pressure in ventilated patients, Critical Care 2005, vol. 9, #5, pp. R562-R568, Available online http://ccforum.com/content/9/5/R562.
Chaoquat, Ari, et al., Association of Chronic Obstructive Pulmonary Disease and Sleep Apnea Syndrome, American Journal Respiratory Critical Care Medicine, 1995, vol. 151, pp. 82-86.
Cherniack and Longobardo, Periodic Breathing During Sleep, pp. 158-190, New Jersey Medical School, Dean's Office, ID 9739727104, May 26, 1999, 14:23, No. 010, (first page missing).
Cherniack, N. S., Introduction to Session on the Pathophysiology of Breathing Control and Breathing: Awake and Asleep, Modeling and Control of Ventilation, Plenum Press, New York, USA, 1995, pp. 87-88.
Cherniack, N. S., New mechanisms for the cardiovascular effects of sleep apnea, American Journal Medicine, Nov. 1, 2000, vol. 109, No. 7, pp. 592-594 (Abstract).
Cherniack, Neil S., Oxygen Sensing: applications in humans, Highlighted Topic: Oxygen Sensing in Health and Disease, Journal Appl. Physiol., vol. 96, pp. 352-358, 2004, The American Physiological Society, http://www.jap.org.
Christiansen, J., et al., Carbon Dioxide in Blood, pp. 266-271, Proceedings of the Physiological Society, This Journal, XLVII, p. ii, 1913, pp. 266-271.
Cilli, Aykut, et al., Nocturnal Oxygen Desaturation in Coronary Artery Disease, JPN Heart Journal, Jan. 1999, pp. 23-28.
CNS Poly G, Printout Examples, CNS, Inc., Chanhassen, Minnesota, USA, Undated, Test Date Feb. 10, 1992.
Conte, G., et al., Acute cardiovascular diseases and respiratory sleep disorders, Minerva Cardioangiol, Jun. 1999, vol. 47, No. 6, pp. 195-202 (Abstract).
Cooper, B. G., et al., Value of Nocturnal Oxygen Saturation as a Screening Test for Sleep Apnoea, Thorax, 1991, vol. 46, pp. 586-588.
Coppola, Michael P., et al., Management of Obstructive Sleep Apnea Syndrome in the Home, The Role of Portable Sleep Apnea Recording, Chest, vol. 104, No. 1, Jul. 1993, pp. 19-24, Northbrook, IL, USA.
Coy, Timothy V., Sleep Apnoea and Sympathetic Nervous System Activity: A Review, Journal Slep Res., 1996, No. 5, pp. 42-50, European Sleep Research Society.
Daley, Denise M., MD, Beware of All Sedatives in Patients With Sleep Apnea, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp, 1997.
Decker, Michael J., et al., Ambulatory Monitoring of Arterial Oxygen Saturation, Chest, vol. 95, No. 4, Apr. 1989, pp. 717-722, Northbrook, Illinois, USA.
Deegan, P. C., et al., Predictive Value of Clinical Features for the Obstructive Sleep Apnoea Syndrome, European Respiratory Journal, vol. 9, pp. 117-124, 1996.
DeLeeuw, P.W., On sleep and death: cardiovascular risk the obstructive sleep apnea syndrome, Neth Journal Medicine, May 1999, vol. 54, No. 5, pp. 188-90 (Abstract).
Dement, William C., Chairman, National Commission on Sleep Disorders Research, Wake Up America: A National Sleep Alert, vol. 1, Executive Summary and Executive Report, Report of the National Commission on Sleep Disorders Research, Submitted to the United States Congress and to the Secretary, u.s. department of Health and Human Services, Jan. 1993, pp. 1-76.
Demeter, P., et al., The relationship between gastroesophageal reflux disease and obstructive sleep apnea, Gastroenterology, Sep. 2004, vol. 39, No. 9, pp. 815-20 (Abstract).
Dempsey, Jerome A., et al., Sleep and Breathing State of the Art Review Sleep/Induced Breathing Instability, Sleep, vol. 19, No. 3, pp. 236-247, American Sleep Disorders Association and Sleep Research Society, Jun. 1998.
Den Herder, Cindy et al., Risks of general anaesthesia in people with obstructive sleep apnea, BMJ, vol. 329, Oct. 23, 2004, pp. 955-959, Downloaded from bmj.com.
Dhonneur, G., et al., Postoperative Obstructive Apnea, Anesth Analg., Sep. 1999, vol. 89, No. 3, pp. 762-767 (Abstract).
Doherty, L. S, et al., Long/term effects of nasal continuous positive airway pressure therapy on cardiovascular outcomes in sleep apnea syndrome, Chest, Jun. 2005, vol. 127, No. 6, pp. 2076-2084 (Abstract).
Douglass, Alan B., et al., The Sleep Disorders Questionnaire I. Creation and Multivariate Structure of SDQ, Clinical Research, Sleep, vol. 17, No. 1, pp. 160-167, 1994 American Sleep Disorders Association and Sleep Research Society.
Dowdell, WT; Javaheri, S; McGinnis, W, Cheyne/Stokes Respiration Presenting as Sleep Apnea Syndrome. Clinical and Polysomnographic Features, Am Rev Respir Dis, Apr 1990, pp. 871-879.
Downs, John B., Has Oxygen Administration Delayed Appropriate Respiratory Care? Fallacies Regarding Oxygen Therapy, Respiratory Care, Jun. 2003, vol. 48, No. 6.
Downs, John B., Is Supplemental Oxygen Necessary, Journal of Cardiothoracic and Vascular Anesthesia, vol. 20, No. 2, Apr. 2006.
Dumas, Constantine, et al., Clinical Evaluation of a Prototype Motion Artifact Resistant Pulse Oximeter in the Recovery Room, Anesth Analg 1996, vol. 83, pp. 269-272.
Dursunoglu, D., et al., Impact of obstructive sleep apnoea on left ventricular mass and global function, European Respiratory Journal, Aug. 2005, vol. 26, No. 2, pp. 283-288 (Abstract).
Dyken, M. E., et al., Obstructive sleep apnea associated with cerebral hypoxemia and death, Neurology, Feb. 10, 2004, vol. 62, No. 3, pp. 491-493 (Abstract).
Dziewas, R., et al., Capnography screening for sleep apnea in patients with acute stroke, Neurology Res. Jan. 2005, vol. 27, No. 1, pp. 83-87 (Abstract).
Dziewas, R., et al., Increased Prevalence of Sleep Apnea in Patients with Recurring Ischemic stroke Compared with First Stroke Victims, Journal Neurology, Nov. 2005, vol. 252, No. 11, pp. 1394-1398. Epub Jul. 20, 2005 (Abstract).
Earthrowl-Gould, T., et al.; "Chest and abdominal surface motion measurement for continuous monitoring of respiratory function," Proc. Instn Mech Engrs, V215, Part H; pp. 515-520 (2001).
East, Christine E., et al.; "Fetal Oxygen Saturation and Uterine Contractions During Labor," American Journal of Perinatology, vol. 15, No. 6, pp. 345-349 (Jun. 1998).
Edge City Hospital Sleep Disorders Center, Sleep Summary of Patient, Houston, Texas, USA, pp. 1-3, Feb. 17, 1997.
Elfadel, I. M., et al., Motion/Resistant Pulse Oximetry, Abstract Only, Journal of Clinical Monitoring, vol. II, No. 4, Jul. 1995, p. 262.
Eihefnawy, Ahmed, et al., Stability Analysis of CO2 Control of Ventilation, Journal of Internal Medicine, 0161/7567/90, pp. 498-503, Publisher: The American Physiological Society, 1990.
Epstein et al., "Cost/Effectiveness Analysis of Nocturnal Oximetry as a Method of Screening for Sleep Apnea/Hypopnea Syndrome," Jan. 1, 1998, Chest, vol. 113, p. 97-103.
Escourrou, P., et al., Heart failure and sleep respiratory disorders. Prevalence, physiopathology and treatment, [Article in French], Rev Mal Respir, Jun. 2000, vol. 17, Suppl 3, pp. S31-S40 (Abstract).
Evans, et al., A Microcomputer System for Monitoring and Analysing Oxyhemolobin Saturation During Sleep. Computer Programs in Biomedicine, 1984; 18: 227-234.
Farhi, Leon E., et al., Dynamics of Changes in Carbon Dioxide Stores, Anesthesiology, Nov./Dec. 1960, vol. 21, pp. 604-614 (last page missing).
Farney, Robert J., et al., Ear Oximetry to Detect Apnea and Differentiate Rapid Eye Movement (REM) and Non/REM (NREM) Sleep, Screening for the Sleep Apnea Syndrome, Chest, vol. 89, No. 4, Apr. 1986, pp. 533-539, Northbrook, IL, USA.
Farre, R., et al., Importance of the Pulse Oximeter Averaging time When Measuring Oxygen Desaturation in Sleep Apnea, Sleep, Jun. 15, 1998, vol. 21, No. 4, pp. 386-390 Missing pp. 386 and 390.
Flinsilver, Steven H., Current and Future Methodology for Monitoring Sleep, Sleep Disorders, Clinics in Chest Medicine, vol. 19, No. 1, Mar. 1998, Published from the Division of Pulmonary Medicine, North Shore University Hospital, Manhasset, New York, NY, USA.
Ferber, Richard, et al., Portable Recording in the Assessment of Obstructive Sleep Apnea, ASDA Standards of Practice, American Sleep Disorders Association, 1610 14th Street, NW, Suite 300, Rochester, MN 55901/2200, USA, 1994.

Findley, Larry J., et al., Cheyne/Stokes Breathing During Sleep in Patients With Left Ventricular Heart Failure, Southern Medical Journal, vol. 78, No. 1, Jan. 1985, pp. 11-15.

Findley, Larry J., et al., Sleep Apnea and Auto Crashes, What is the Doctor to do?, Chest, vol. 94, No. 2, Aug. 1988, pp. 225-226.

Fisher, Kyle S., MD, Value of Pulse Oximetry Monitoring on the Ward is Questioned, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp, 2002.

Fiz, J. A., et al., Acoustic Analysis of Snoring Sound in Patients with Simple Snoring and Obstructive Sleep Apnoea, European Respiratory Journal, 1996, vol. 9, pp. 2365-2370, Printed in the United Kingdom.

Flemons, W. Ward, et al., Sleep Apnea and Cardiac Arrhythmias, Is There a Relationship?, American Review Respiratory Disease, vol. 148, pp. 618-621, 1993.

Fletcher et al., Effect of Cardiac Output Reduction on Rate of Desaturation in Obstructive Apnea; Chest, 99:452-456, 1991.

Fletcher et al., Rate of Oxyhemolglobin Desaturation in Obstructive versus Nonobstructive Apnea; Am Rev Respi Dis. 143:657-660; 1990.

Fletcher et al., The Rate of Fall of Arterial Oxyhemoglobin Saturation in Obstructive Sleep Apnea, Chest, 1989; 96: 717-722.

Fletcher, Eugene C., et al., Nocturnal Oxyhemoglobin Desaturation in COPD Patients with Arterial Oxygen Tensions Above 60 mm Hg, Chest, vol. 92, No. 4, Oct. 1987, pp. 604-608.

Forster, R. E., et al., Time course of exchanges between red cells and extracellular fluid during $CO_2$ uptake, Journal of Applied Physiology, vol. 38, No. 4, Apr. 1975, Printed in U.S.A.

Forster, Robert E., The Lung: Physiologic Basis of Pulmonary Function Tests (Book), 1986 Year Book medical Publishers, Inc., Chapter 3, I. Volume of Pulmonary Ventilation, pp. 32-64.

Franklin, K. A., et al., Reversal of Central Sleep Apnea with Oxygen, Chest, Jan. 1997, vol. 111, No. 1, pp. 163-169 (Abstract).

Freid, E. B. The rapid sequence induction revisited: obesity and sleep apnea syndrome, Anesthesiol . Clin North America, Sep. 2005, vol. 23, No. 3, pp. 551-564 (Abstract).

Frumin, Jack M., Apneic Oxygenation in Man, Anesthesiology, vol. 20, pp. 789-798, 1959.

Fu, Eugene S., et al., Supplemental Oxygen Impairs Detection of Hypoventilation by Pulse Oximetry, Chest 2004; vol. 126, pp. 1552-1558.

Gagnadoux, Fredrick et al., Home Unattended vs Hospital Telemonitored Polysomnography in Suspected Obstructive Sleep Apnea Syndrome: A Randomized Crossover Trial, Chest 2002; 121; 753-758.

Gami, A. et al., Day/night pattern of sudden death in obstructive sleep apnea, New England Journal Medicine, Mar. 24, 2005, vol. 352, No. 12, pp. 1206-1214.

Gangitano, E. S., et al., Near Continuous Pulse Oximetry During Newborn ECLS, ASAI Journal, 1999, vol. 45, No. 1, p. 125 (Abstract).

Gaultier, C., Upper airway muscles and physiopathology of obstructive sleep apnea syndrome, [Article in French], Neurophysiol Clin, Jun. 1994, vol. 24, No. 3, pp. 195-206 (Abstract).

Gavin, T. P., et al., The effect of exercise modality on exercise/induced hypoxemia, Respiration Physiology, May 3, 1999, vol. 115, No. 3, pp. 317-323 (Abstract).

Gentil, Benoit, et al., Enhancement of Postoperative Desaturation in Heavy Snorers, Anesth Analg 1995, vol. 81, pp. 389-392.

George et al., Identification on Qualification of Apneas by Computer/based Analysis of Oxygen Saturation, American Review of Respiratory Disease, 1988; 137; 1238-1240.

George, Charles Frederick Petersen, Diagnostic Techniques in Obstructive Sleep Apnea, Progress in Cardiovascular Diseases, vol. 41, No. 5, Mar./Apr. 1999, pp. 355-366.

Glerant, J. C., et al., Intensive care and respiratory sleep disorders, [Article in French], Rev Mal Respir, Dec. 1999, vol. 16, No. 6, pp. 1091-104 (Abstract).

Gold, Avram R., et al., Impact of Basic Research on Tomorrow's Medicine, The Pharyngeal Critical Pressure, The Whys and Hows of Using Nasal Continuous Positive Airway Pressure Diagnostically, Chest, vol. 110, No. 4, Oct. 1996, pp. 1077-1088, Northbrook, IL, USA.

Goldberger, Ary L., et al., Components of a New Research Resource for Complex Physiologic Signals, PhysioBank, PhysioToolkit, and PhysioNet, American Heart Association Journals, Circulation, vol. 101, No. 23, pp. 1-9, 2000, Circulation, 2000:101:e215, http://circ.ahajournals.org/cgi/content/ful/101/23/e215.

Goldstein, M. R., et al., Pulse Oximetry in Transport of Poorly/Perfused Babies, Abstract only, Pediatrics, 1998, vol. 102, No. 3, p. 818.

Goode, Richard L., Who needs a sleep test? The value of the history in the diagnosis of obstructive sleep apnea, http://www.findarticles.com/p/articles/mi_m0BUM/is_9_78/ai_56229331/print, Sep. 1999.

Goodfriend, Theodore L., et al., Resistant Hypertension, Obesity, Sleep Apnea, and Aldosterone: Theory and Therapy, Hypertension, Journal of the American Heart Association, published online Jan. 19, 2004, Print ISSN: 0194-911X. Online ISSN: 1524/4563, pp. 518-524, Dallas, Texas, USA.

Grap, Mary Jo, Protocols for Practice, Applying Research at the Bedside, Critical Care Nurse, vol. 18, No. 1, Feb. 1998, pp. 94-99.

Greco, J. M., et al., Long/term Airway Space Changes after Mandibular Setback Using Bilateral Sagittal Split Osteomy, Internal Journal Oral Maxillofac. Surg. 1990, vol. 19, pp. 103-105.

Greco, Joan M., Cephalometric Analysis of Long/Term Airway Space Changes with Maxillary Osteotomies, Oral Surg Oral Med Oral Pathol, Nov. 1990, vol. 70, No. 5, pp. 552-554.

Griffiths, et al., A Video System for Investigating Breathing Disorders During Sleep, Thorad, 1991; 46: 136-140.

Grimm, W., et al., Outcome of patients with sleep apnea/associated severe bradyarrhythmias after continuous positive airway pressure therapy, American Journal Cardiology, Sep. 15, 2000, vol. 86, No. 6, pp. 688-692 (Abstract).

Grote, Ludger, et al., Finger Plethysmography—A Method for Monitoring Finger Blood Flow During Sleep Disordered Breathing, Respiratory Physiology & Neurobiology, vol. 136, 2003, pp. 141-152, Publisher: Elsevier.

Grunstein, Ronald R., et al., Treatment of Sleep Disordered Breathing, Position Statement, The Medical Journal of Australia, vol. 154, Mar. 4, 1991, pp. 355-359, Australia.

Gugger, M., Comparison of ResMed AutoSet (version 3.03) with polysomnography in the diagnosis of the sleep apnoea/hypopnoea syndrome, European Respiratory Journal, Mar. 1997, vol. 10, No. 3, pp. 587-91 (Abstract).

Guilleminault et al., Sleep Apnea Syndrome: Can It Induce Hemodynamic Changes?, Western Journal of Medicine, vol. 123, Jul. 1975, pp. 7-16.

Guilleminault, C. et al., Unattended CPAP Titration: Toward a Smart Machine, May 20, Stanford University Sleep Research Center, 1 page, 2001.

Guilleminault, C., et al., Maxillo/mandibular surgery for obstructive sleep apnoea, European Respiratory Journal, 1989, vol. 2, pp. 604-612.

Guilleminault, C., et al., Sleep/disordered breathing in children, Annals of Medicine, vol. 30, No. 4, pp. 350-356, Aug. 1998 (Abstract).

Guilleminault, Christian, et al., A Cause of Excessive Daytime Sleepiness, The Upper Airway Resistance Syndrome, Chest, vol. 104, No. 3, Sep. 1993, pp. 781-787.

Guilleminault, Christian, et al., the Sleep Apnea Syndromes, Copyright 1976, Citation Annual Review of Medicine, vol. 27: 465-484 (vol. publication date Feb. 1976).

Guilleminault, Christian, Obstructive Sleep Apnea, The Clinical Syndrome and Historical Perspective, Medical Clinics of North America, vol. 69, No. 6, Nov. 1985, pp. 1187-1203, Stanford, California, USA.

Gupta, R. M., et al., Perioperative cardiopulmonary evaluati and management: are we ignoring obstructive sleep apnea syndrome?, chest, Dec. 1999, vol. 116, No. 6, p. 1843 (Abstract).

Gupta, Rakesh M., et al., Postoperative Complications in Patients with Obstructive Sleep Apnea Syndrome Undergoing Hip or Knee Replacement: A Case/Control Study, Mayo Clinic Proceedings, 2001, vol. 76, pp. 897-905, Rochester, MN, USA.

Gyulay et al., A Comparison of Clinical Assessment and Home Oximetry in the Diagnosis of Obstructive Sleep Apnea, American Review of Respiratory Disease, 1993; 147: 50-53.

Gyulay, Stephen, et al., Evaluation of a Microprocessor/Based Portable Home Monitoring System to Measure Breathing During Sleep, Sleep, vol. 10, No. 2, pp. 130-142, Raven Press, New York, USA, 1987, Association of Professional Sleep Societies.

Hanley, Patrick, et al., Pathogenesis of Cheyne/Stokes Respiration in Patients with Congestive Heart Failure, Relationship to Arterial $Pco_2$, Chest, vol. 104, No. 4, Oct. 1993, pp. 1079-1084.

Hanly, P. J., et al., Increased Mortality Associated with Cheyne/Stokes Respiration in Patients with Congestive Heart Failure, American Journal Respiratory Critical Care Medicine, Jan. 1996, vol. 153, No. 1, 272-6 (Abstract).

Hanly, Patrick J., et al., Respiration and Abnormal Sleep in Patients with Congestive Heart Failure, Chest, vol. 96, No. 3, Sep. 1989, pp. 480-488.

Hanly, Patrick, et al., ST/Segment Depression During Sleep in Obstructive Sleep Apnea, The American Journal of Cardiology, vol. 71, Jun. 1, 1993, pp. 1341-1345.

Harbison, J., et al., Cardiac rhythm disturbances in the obstructive sleep apnea syndrome: effects of nasal continuous positive airway pressure therapy, Chest, Sep. 2000, vol. 118, No. 3, pp. 591/ (Abstract).

Hatta, K., et al., Prolonged upper airway instability in the parenteral use of benzodiazepine with levomepromazine, Journal Clin Psychopharmacol, Feb. 2000, vol. 20, No. 1, pp. 99/ (Abstract).

He: Jiang, et al., Mortality and Apnea Index in Obstructive Sleep Apnea, Experience in 385 Male Patients, Clinical Investigations, Chest, vol. 94, No. 1, Jul. 1988, pp. 9-14.

Health Devices, Next/Generation Pulse Oximetry, Special Issue, Feb. 2003, vol. 32, No. 2, Plymouth Meeting, PA, USA.

Henderson, L. J., et al., Blood as a Physicochemical System. II, pp. 426-431, Paper, 1921.

Hillman, David R., et al., Obstructive Sleep Apnoea and Anaesthesia, Sleep Medicine Reviews, 2004, vol. 8, pp. 459-472, Publisher: Elsevier.

Hoch, et al., Uberprufung der Fruherkennungsmethode MESAM and Biox 3700 zur Erfassung Schlafbezogener Atmmgmsergulationsstorungen bei jungen Mannern, Pneumologie, 1991; 45: 217-222 (and translation).

Hoffarth, et al., Beuteilung Pulsoximetrisch Erfasster zklisheer.. and translation (Hoffarth et al. Assessment of Cyclic and Phasic Oxygen Desaturations Measured via Pulsoxymetry in Nocturnal Diagnosis of Respiratory Regulation Disorders, Peumologie, May 1991; 45: 229-232.

Hoffman, Eric A., et al., Multimodality Imaging of the Upper Airway: MRI, MR Spectroscopy, and Ultrafast X/ray CT, Sleep and respiration, 1990 Wiley/Liss, Inc., pp. 291-301.

Hoffmann, M., et al., Sleep apnea and hypertension, Minerva Med., Aug. 2004, vol. 95, No. 4, pp. 281-290 (Abstract).

Hoffstein, Victor, Blood Pressure, Snoring, Obesity, and Nocturnal Hypoxaemia, The Lancet, vol. 344, Sep. 3, 1994, pp. 643-645.

Hoffstein, Victor, et al., Cardiac Arrhythmias, Snoring, and Sleep Apnea, Chest, 1994, vol. 106, pp. 466-471, Northbrook, IL, USA.

Hoffstein, Victor, et al., Snoring and Arousals: A Retrospective Analysis, Sleep, vol. 18, No. 10, pp. 866-82, 1995 American Sleep Disorders Association and Sleep Research Society.

Holmes, Michael, et al., Co/Oximetry Validation of a New Pulse Oximeter in Sick Newborns, Respiratory Care, 1998, vol. 43, No. 10, pp. 860 (Abstract).

Howell, Mandy et al.; *Pulse oximetry: an audit of nursing and medical staff understanding*; British Journal of Nursing, 2002, vol. 11, No. 3; pp. 191-197.

Hornero, Roberto, et al.; "Utility of Approximate Entropy From Overnight Pulse Oximetry Data in the Diagnosis of the Obstructive Sleep Apnea Syndrome,"; IEEE Transactions on Biomedical Engineering, vol. 54, No. 1, pp. 107-113, Jan. 2007.

Hung, Joseph, et al., Association of Sleep Apnoea with Myocardial Interfarction in Men, The Lancet, vol. 336, pp. 261-264, Jul. 28, 1990, Abstract only, p. 261.

Isono, S., et al., Anatomy of pharynx in patients with obstructive sleep apnea and in normal subjects, Journal Appl Physiol, Apr. 1997, vol. 82, No. 4, pp. 1319-1326 (Abstract).

Isono, S., et al., Interaction of cross/sectional area, driving pressure, and airflow of passive velopharynx, Journal Appl Physiol, Sep. 1997, vol. 83, No. 3, pp. 851-859 (Abstract).

Isono, S., et al., Static mechanics of the velopharynx of patients with obstructive sleep apnea, Journal Appl Physiol, Jul. 1999, vol. 75, No. 1, pp. 148-54 (Abstract).

Jain, Sanjay S., et al., Perioperative Treatment of Patients with Obstructive Sleep Apnea, Current Opinion Pulmonary Medicine 10, pp. 482-488, 2004.

Jarrell, L., Preoperative diagnosis and postoperative management of adult patients with obstructive sleep apnea syndrome: a review of the literature, Journal Perianesth Nursing, Aug. 1999, vol. 14, No. 4, pp. 193-200 (Abstract).

Javaheri, S., Effects of continuous positive airway pressure on sleep apnea and ventricular irritability in patients with heart failure, Circulation, Feb. 1, 2000, vol. 101, No. 4, pp. 392-397 (Abstract).

Javaheri, S., et al., Occult Sleep/Disordered Breathing in Stable Congestive Heart Failure, Annuals Internal Medicine, Apr. 1995, vol. 122, No. 7, pp. 487-492 (Abstract).

Javaheri, S., et al., Sleep Apnea in 81 Ambulatory Male Patients With Stable Heart Failure, Types and Their Prevalences, Consequences, and Presentations, Received Nov. 20, 1997; revision received Jan. 23, 1998, accepted Jan. 28, 1998, From the Sleep Disorders Laboratory, Department of Veterans Affairs Medical Center, and the Department of Medicine, University of Cincinatti, College of Medicine, Cincinnati, Ohio.

Johansson, A.; "Neural network for photoplethysmographic respiratory rate monitoring," Medical & Biological Engineering & Computing, vol. 41, pp. 242-248 (2003).

Johnston, W.S., et al.; "Extracting Breathing Rate Infromation from a Wearable Reflectance Pulse Oximeter Sensor," Proceedings of the 26th Annual International conference of the IEEE EMBS, San Francisco, California; Sep. 1-5, 2004; pp. 5388-5391.

Johnson, J. T., et al., Preoperative, Intraoperative, and postoperative management of patients with obstructive sleep apnea syndrome, Otolaryngol Clin North America, Dec. 1998, vol. 31, No. 6, pp. 1025-1030 (Abstract).

Jones, N. L. et al., The Estimation of Carbon Dioxide Pressure of Mixed Venous Blood During Exercise, Clinical Science (1967), vol. 32, pp. 311-327.

Juhász, János, et al., Unattended Continuous Positive Airway Pressure Titration, Clinical Relevance and Cardiorespiratory Hazards of the Method, American Journal Respiratory Critical Care Medical, vol. 154, pp. 359-365, 1996.

Kabeli, Cheryl, Obstructive Sleep apnea and Modifications in Sedation, Critical Care Nursing Clinics of North America, vol. 17, 2005, pp. 269-277, ccnursing.theclinics.com, Publisher: Elsevier Saunders.

Kalra, Maninder, et al., Obstructive Sleep Apnea in Extremely Overweight Adolescents Undergoing Bariatric Surgery, Obesity Research, vol. 13, No. 7, Jul. 2005, pp. 1175-1179.

Kanagala, Ravi, et al., Obstructive Sleep Apnea and the Recurrence of Atrial Fibrillation, Circulation, May 27, 2003, pp. 2589-2594, American Heart Association, Inc.

Kaplan, Joseph, Beginner's Atlas of Overnight Oximetry, Apr. 10, 1995, Mayo Clinic, Jacksonville, Florida, USA, Copyright 1986, PROFOX Associates, Inc.

Kaplan, Joseph, et al., Home Pulse Oximetry as a Screening Test for Sleep/Disordered Breathing, Chest, vol. 103, pp. 322S, (1993) Northbrook, IL, USA.

Kapur, V. K., et al., Association of hypothyroidism and obstructive sleep apnea, American Journal of Respiratory & Critical Care Medicine, vol. 158, No. 5 Pt. 1, pp. 1379-1383, Nov. 1998 (Abstract).

Kapur, V., et al., The medical cost of undiagnosed sleep apnea, Sleep, Sep. 1999, vol. 22, No. 6, pp. 749-755 (Abstract).

Katchen, Marc, et al., Evaluation of the Sleepy Crewmember: USAFSAM Experience and a Suggested Clinical Approach, Aviation, Space and Environmental Medicine, Mar. 1989, pp. 263-267.

Kaw, Roop, et al., Unrecognized Sleep Apnea in the Surgical Patient, Implications for the Perioperative Setting, Chest, 2006, vol. 129, pp. 198-205.

Kawai, Mitsuru, et al., Nocturnal hypoxia index: A new pulse oxymetry index of nocturnal hypoventilation in neuromuscular disorders, Clinical Neurology, vol. 35, pp. 1003-1007, 1995 (Abstract).

Keyl, C. et al., Spektralanalyse von Arterieller Sauerstoff/sättigung and RR/Intervallen bei Patienten mit obstrulutver Schlafapnoe, Wein Med Wschr 1995, pp. 515-516 (vol. 145).

Kimmel, Paul L., et al., Sleep Apnea syndrome in Chronic renal Disease, The American Journal of Medicine, vol. 86, Mar. 1989, pp. 308-314.

King, E. D., et al., A model of obstructive sleep apnea in normal humans. Role of the upper airway., American Journal Respiratory Critical Care Medicine, Jun. 2000, vol. 161, No. 6, pp. 1979-1984 (Abstract).

Kirby et al., Computer Quantitation of Saturation Impairment Time as an Index of Oxygenation During Sleep, Com Meth, 1992: 107-115.

Kirby, S.D., et al., Neural network prediction of obstructive sleep apnea from clinical criteria, Chest, vol. 116, No. 2, pp. 409-415, Aug. 1999 (Abstract).

Kirby, Stan C., et al., Section II. Systems and programs, Computer quantitation of saturation impairment time as an index of oxygenation during sleep, Computer Methods and Programs in Biomedicine, vol. 38, 1992, pp. 107-115, Elsevier Science Publishers B.V.

Klocke, F. J., et al., Breath holding after breathing of oxygen, Journal Appl. Physiol., vol. 14, No. 5, pp. 689-693, 1959.

Koehler, U., et al., Heart Block in Patients with Obstructive Sleep Apnoea: Pathogenetic Factors and Effects of Treatment, European Respiratory Journal, 1998, vol. 11, pp. 434-439, Printed in United Kingdom.

Koehler, U., et al., Nocturnal Myocardial Ischemia and Cardiac Arrhythmia in Patients with Sleep Apnea with and Without Coronary Heart Disease (1991) 69; 474-482.

Kolobow, Theodor, et al., Intratracheal Pulmonary Ventilation (ITPV); Control of Positive End/Expiratory Pressure at the Level of the Carina Through the Use of a Novel ITPV Catheter Design, Anesth Analg, 1994 , vol. 78, pp. 455-461.

Koopmann, Charles F., et al., Surgical Management of Obstructive Sleep Apnea, Otolaryngologic Clinics of North America, vol. 23, No. 4, Aug. 1990, pp. 787-808.

Krachman, S. L., et al., Comparison of oxygen therapy with nasal continuous positive airway pressure on Cheyne/Stokes respiration during sleep in congestive heart failure, Chest, Dec. 1999, vol. 116, No. 6, pp. 1550-1557 (Abstract).

Kribbs, Nancy Barone, et al., Effects of One Night without Nasal CPAP Treatment on Sleep and Sleepiness in Patients with Obstructive Sleep Apnea, American Review Respiratory Disease, vol. 147, pp. 1162-1168, 1993.

Kribbs, Nancy Barone, et al., Objective Management of Patterns of Nasal CPAP Use by Patients with Obstructive Sleep Apnea, American Review Respiratory Disease, vol. 147, pp. 887-895, 1993.

Krieger, Jean, et al., Breathing During Sleep in Normal Middle/Aged Subjects, Sleep, vol. 13, No.2, pp. 143-154, Raven Press, Ltd. New York, NY, USA, 1990 Association of Professional Sleep Societies.

Krieger, Jean, et al., Left Ventricular Ejection Fraction in Obstructive Sleep Apnea, Effects of Long/term Treatment with Nasal Continuous Positive Airway Pressure, Chest, vol. 100, No. 4, Oct. 1991, pp. 917-921.

Krieger, Jean., et al., Dangerous Hypoxaemia During Continuous Positive Airway Pressure Treatment of Obstructive Sleep Apnoea, The Lancet, Dec. 17, 1983, pp. 1429-1430.

Kuna, S. T., et al., Pathophysiology of upper airway closure during sleep, JAMA, Sep. 11, 1991, vol. 266, No. 10, pp. 1384-1389 (Abstract).

Kyzer, S., et al., Obstructive Sleep Apnea in the obese, World Journal Surg, Sep. 1988, vol. 22, No. 9, pp. 998-1001 (Abstract).

Lafontaine, Victoria M., et al., Pulse Oximetry: Accuracy of Methods of Interpreting Graphic Summaries, Pediatric Pulmonology, vol. 21, 1996, pp. 121-131.

Lanfranchi, P. A., et al., Prognostic value of nocturnal Cheyne/Stokes respiration in chronic heart failure, Circulation, Mar. 23, 1999, vol. 99, No. 11, pp. 1435-40, Italy (Abstract).

Lanfranchi, P., et al., The assessment of breathing during sleep: a curiosity or clinical necessity?, Italian Heart Journal, May 2000, vol. 1, No. 5 Suppl., pp. 641-654 (Abstract).

Lawrence, Nancy, Treatment for Sleep Apnea shows promise in reducing deaths from congestive heart failure: Nation/wide study to determine long/term benefits, London Health Sciences Centre, Jun. 3, 1999, News Bulletin.

Lertzman, Morley, et al., [Letters—Correspondence], Sleep Apnea A Risk Factor for Poor Driving, Canadian Medical Association Journal, Oct. 15, 1995; vol. 153(8), p. 1063.

Letters, Obstructive Sleep Apnoea, BMJ, 1997, pp. 315-367 (Aug. 9); http://bmj.com/Shneerson et al. (7104).

Lichstein, K. L., et al., Occult sleep apnea in a recruited sample of older adults with insomnia, Journal of Consulting & Clinical Psychology, vol. 67, No. 3, pp. 405-410, Jun. 1999 (Abstract).

Little, S. A., et al., Predictors of nocturnal oxygen desaturation in patients with COPD, Respir Med., Mar. 1999, vol. 93, No. 3, pp. 202-207, United Kingdom (Abstract).

Lofsky, Ann, Sleep Apnea and Narcotic Postoperative Pain Medication: A Morbidity and Mortality Risk, APSF Newsletter Summer 2002, pp. 24-25.

Longobardo et al., Sleep Apnea Considered as a Control System Instability, Sep. 1982, Respiratory Physiology 50: 311-333.

Longobardo, G. S., et al., Sleep Apnea Considered as a Control System Instability, Elsevier Biomedical Press, 1982, 0034/5687/82/0000/0000.

Lowton, K., Pulse oximeters for the detection of hypoxaemia, Professional Nurse, Feb. 1999, vol. 14, No. 5, pp. 343-347 (Abstract).

Lugaresi, E., et al., Breathing During sleep in Man in Normal and Pathological Conditions, Proceedings of the Symposium on Regulation of Respiration during Sleep and Anesthesia held at the Faculte de Medecine Saint/Antoine, Paris, France, Jul. 14/16, 1977, 1978 Plenum Press, New York, USA, pp. 35-45.

Lynn, Lawrence A. et al., Diagnostic Evaluation of OSA Utilizing Analysis of Frequency and Spatial Relationships of Clustered, Sequential Oximetry Waveform Events, Vth World Congress on Sleep Apnea, Marburg, Germany, Sep. 17-20, 1997.

C229LYNN, Lawrence A., Cluster Analysis: A New Technology for the Evaluation of Oximetry and Airflow Waveforms in Obstructive Sleep Apnea, Accepted after revision on Dec. 20, 1997, 17 total pages.

Lynn, Lawrence, Profox Associates, Inc., Version 12S (12 hours SpO2), Demonstration disk for Dr. Lawrence Lynn, Columbus, Ohio, Copyright 1986 PROFOX Associates, Inc., Version 12S, 11-92, p. 1.

Lynn, Lawrence A., Interpretive Oximetry: Future Directions for Diagnostic Applications of the Sp02 Time/Series, Anesth Analg 2002, vol. 94, pp. S84-S88.

Lynn, Lawrence; *Piercing the Panacea of Pulse Oximetry*; The Sleep and Breathing Research Institute, Columbus, Ohio, US, 2002.

Lyznicki, James M., Sleepiness, Driving and Motor Vehicle Crashes, JAMA, Jun. 17, 1998, vol. 279, No. 23, pp. 1908-1913.

Mackenzie, I.M.J.; *The haemodynamics of human septic shock*; Anaesthesia; 2001; 56; pp. 130-144; UK.

Magalang, Ulysses J. et al., Prediction of the Apnea/Hypopnea Index From Overnight Pulse Oximetry, Chest the Cardiopulmonary and Critical Care Journal, 2003; vol. 124; pp. 1694-1701, Northbrook, IL, USA.

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Manley,G.T.; Cerebral Oxygenation During Hemorrhagic Shock: Perils of Hyperventilation and the Therapeutic Potential of Hypoventilation, *J Trauma*: 2000; 48: 1025-1032.

Marin, José M., et al., Obstructive Sleep Apnea and Acute Myocardial Infarction: Clinical Implications of the Association, Sleep, vol. 21, No. 8, 1998, pp. 809-815.

Marin, Jose M., et al., Long/Term Cardiovascular Outcomes in Men with Obstructive sleep apnoea/hypopnoea with or without treatment with continuous positive airway pressure: an observational study, The Lancet, vol. 365, Issue 9464, Mar. 19, 2005/Mar. 25, 2005, pp. 1046-1053.

Mayer, Pierre, et al., Peripheral Neuropathy in Sleep Apnea, A Tissue Marker of the Severity of Nocturnal Desaturation, American Journal Respiratory Critical Care Medicine, vol. 159, pp. 213-219, 1999, Internet address: www.atsjournals.org.

McDannold, M. D., et al., Night/to/Night variability in Optimal CPAP Pressures Using Auto CPAP Titration in a Single Patient, Sleep Research No. 23, 1994, p. 453 (Abstract).

McEvoy, R. D., et al., Ventilatory responses to sustained eucapnic hypoxia in healthy males during wakefulness and NREM sleep, Sleep, vol. 20, No. 11, Nov. 1997, pp. 1008-1011 (Abstract).

McGregor, Christine D. et al., Performance of Pulse Oximeter Technologies in a Pediatric Sleep Lab Setting, OF/901-191, dated Nov. 2, 2001, Abstract.

McNicholas, W. T., et al., Diagnostic Criteria for the Sleep Apnoea Syndrome: Time for Consensus?, European Respiratory Journal, vol. 9, pp. 634-635, 1996, United Kingdom.

Mehra, Reena, et al., Association of Nocturnal Arrhythmias with Sleep/Disordered Breathing: The Sleep Heart Health Study, AJRCCM Articles in Press, Published Jan. 19, 2006, as doi: 10.1164/rccm.200509/1442OC, Copyright 2006 by the American Thoracic Society.

Mehta, Y., et al., Obstructive sleep apnea syndrome: anesthetic implications in the cardiac surgical patient, Journal Cardiothorac Vasc Anesth, Aug. 2000, vol. 14, No. 4, pp. 449-453 (Abstract).

Mendelson, W. B., et al., Effects of Hemodialysis on Sleep Apnea Syndrome in End/Stage Renal Disease, Clinical Nephrology, vol. 33, No. 5, 1990, pp. 247-251.

Middlekoop, Huub, et al., The Value of Nocturnal Motor Activity Monitoring as a Screening Tool for Obstructive Sleep Apnoea, Letter to the Editor, Journal Sleep Res., 1996, vol. 5, pp. 66-67.

Miles, L. E., et al., Development and Application of Automatic Nasal CPAP Calibration Procedures for Use in the Unsupervised Home Environment, Sleep, vol. 16, pp. S118-S119, 1993 American Sleep Disorders Association and Sleep Research Society.

Miles, Laughton E., Optimization of Nasal/CPAP Airflow Pressure by Use of Home Oximetry Recordings, Clinical Monitoring Center, Palo Alto, California, USA, Sleep Research, p. 568, 1987, Abstract.

Millard, R. K., Inductive plethysmography components analysis and improved non/invasive postoperative apnoea monitoring, Physiol Meas, May 1999, vol. 20, No. 2, pp. 175-86, United Kingdom (Abstract).

Mitler, Merrill M., et al., Narcolepsy and Its Treatment With Stimulants, ASDA Standards of Practice, Sleep, vol. 17, No. 4, pp. 352-371, 1994, American Sleep Disorders Association and Sleep Research Society.

Miyamura, Miharu, et al., $CO_2$ Dissociation Curves of Oxygenerated Whole Blood Obtained at Rest and in Exercise, European Journal Applied Physiology, vol. 39, pp. 37-45, 1978, European Journal of Applied Physiology and Occupation Physiology.

Moller, J.T. et al.; *Hypoxaemia is Reduced by Pulse Oximetry Monitoring in the Operating Theatre and in the Recovery Room*; British Journal of Anaesthesia; 1992; vol. 68; pp. 146-150.

Moller, Jakob T. et al.; *Randomized Evaluation of Pulse Oximetry in 20,802 Pateints: I*; Anesthesiology, vol. 78, No. 3; Mar. 1993; pp. 436-444; US.

Moller, Jakob T. et al.; *Randomized Evaluation of Pulse Oximetry in 20,802 Patients: II*; Anesthesiology, vol. 78, No. 3; Mar. 1993; pp. 445-453; US.

Morelot/Panzini, Capucine et al., Simplified Method to Measure Respiratory/Related Changes in Arterial Pulse Pressure in Patients Receiving Mechanical Ventilation, Chest 2003, vol. 124, pp. 665-670, Northbrook, IL, USA.

Muller, Nestor L., et al., Mechanism of Hemoglobin Desaturation During Rapid/Eye/Movement Sleep in Normal Subjects and in Patients with Cystic Fibrosis, American Review of Respiratory Disease, vol. 121, 1980, pp. 463-469.

Murray, Carol B. et al.; *Making the most of pulse oximetry*; Contemporary Pediatrics; Jul. 1995; pp. 45-62.

Myatt, H. M., et al., Snoring—a simple surgical solution, Clin. Otolaryngol., 1996, vol. 21, pp. 419-424, Publisher: Blackwell Science Ltd.

Narkiewicz, Krzysztof, et al., Altered Cardiovascular Variability in Obstructive Sleep Apnea, Copyright 1998, American Heart Association, Inc., Iowa City, Iowa, USA, pp. 1071-1077, Published Sep. 15, 1998.

Naughton, Matthew T., et al., Sleep Apnea in Congestive Heart Failure, Clinics in Chest Medicine, vol. 19, No. 1, Mar. 1998, pp. 99-113.

Naughton, Matthew T., Cycling Sleep Apnea, The Balance of Compensated and Decompensated Breathing, American Journal of Respiratory and Critical Care Medicine, vol. 168, 2003, Editorials, pp. 624-625.

Neuman, Michael R.; *Pulse Oximetry: Physical Principles, Technical Relization and Present Limitations*; Adv Exp Med Biol 1987;220; pp. 135-144.

Neumann, Cristina et al., Nocturnal oxygen desaturation in diabetic patients with severe autonomic neuropathy, Diabetes Research and Clinical Practice, Publisher: Elsevier Science Ireland Ltd, vol. 28, 1995, pp. 97-102.

Netzer, Nikolaus, et al., Overnight Pulse Oximetry for Sleep/Disordered Breathing in Adults, A Review, Chest, vol. 120, #2, Aug., 2001, pp. 625-633, Northbrook, IL, USA.

Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).

Nobili, L., et al., Morning increase of whole blood viscosity in obstructive sleep apnea syndrome, Clinical Hemorheol Microcirc, 2000, vol. 22, No. 1, pp. 21-27 (Abstract).

Noda, A., et al., Daytime sleepiness and automobile accidents in patients with obstructive sleep apnea syndrome, Psychiatry & Clinical Neurosciences, vol. 52, No. 2, pp. 221-222, Apr. 1988 (Abstract).

Noda, Akiko, et al., Circadian Rhythm of Autonomic Activity in Patients with Obstructive Sleep Apnea Syndrome, Clinical Cardiology, vol. 21, pp. 271-276, 1998, Japan.

O'Donovan, Richard et al.; *Acid/Base Disturbances in Cardiogenic Polmonart Edema*; Nephron; 1991; 57; pp. 416-420.

Ogan, O. U., et al., Anesthetic safety always an issue with obstructive sleep apnea, Journal Clin Monit Comput, Jan. 1998, vol. 14, No. 1, pp. 69-70 (Abstract).

Ogretmenoglu, O., et al., Body fat composition: a predictive factor for obstructive sleep apnea, Laryngoscope, Aug. 2005, vol. 115, No. 8, pp. 1493-1498 (Abstract).

Ohga, Eijiro, et al., Increased Levels of Circulating ICAM/1, VCAM/1, and L/selectin in obstructive sleep apnea syndrome, Address for reprint requests and other correspondence: T. Nagase, Dept. of Geriatric Medicine, Faculty of Medicine, Univ. of Tokyo, 7/3/1, Hongo, Bunkyo/Ku, Tokyo 113, Japan, Received Nov. 13, 1998, accepted in final form Mar. 9, 1999.

Olson, L. G., et al., Prediction of Sleep/disordered breathing by unattended overnight oximetry, Journal Sleep Res., 1999, vol. 8, pp. 51-55, European Sleep Research Society.

Olson, Leslie G., et al., Chapter 10, A Biomechanical View of Upper Airway Function, pp. 359-389, 1988, Publisher, Marcel Dekker, Inc., New York—Basel, Book: Respiratory Function of the Upper Airway.

Ostermeier, A. M. et al. Three sudden postoperative respiratory arrests associated with epidural in opioids in patients with sleep apnea, Anasth Analg., Aug. 1997, vol. 85, No. 2, pp. 452-460.

Owen, G. O., et al., Overnight Pulse Oximetry in Normal Children and in Children Undergoing Adenotonsillecomy, Clinical Otolaryngology, 1996 vol. 21, pp. 59-65, Blackwell Science Ltd.

Owen, G. O., et al., Overnight Pulse Oximetry in Snoring and Non/Snoring Children, Clinical Otolaryngology, 1995, vol. 20, pp. 402-406, Blackwell Science Ltd.

OxiScan, AirSep Corporation, 800-874/0202, Oxiscan Sample Report/Explanation and the Delta Sleep Apnea Index, OxiScan Sample Report, vol. 1, Rev. 01, Nov. 1997.

Pae, E. K., et al., Intermittent hypoxia damages cerebellar cortex and deep nuclei, Neurosci Lett., Feb. 28, 2005, vol. 375, No. 2, pp. 123-128 (Abstract).

Partinen, Markku, et al., Daytime Sleepiness and Vascular Morbidity at Seven/Year Follow/up in Obstructive Sleep Apnea Patients, Chest, vol. 97, No. 1, Jan. 1990, pp. 27-32.

Patil, Ramesh S. et al., Application of an Artificial Intelligence Program to Therapy of High/Risk Surgical Patients, New Horizons, vol. 4, No. 4, pp. 541-550, 1988.

Payne, J. P., Apnoeic Oxygenation in Anaesthetised Man, Acta Anaesth. Scandinav., 1962, vol. 6, pp. 129-142.

Peker, Y. et al., An independent association between obstructive sleep apnoea and coronary artery disease, European Respiratory Journal, 1999, vol. 14, No. 1, pp. 179-184 (Abstract).

Peker, Y., et al., Reduced hospitalization with cardiovascular and pulmonary disease in obstructive sleep apnea patients on nasal CPAP treatment, Sleep, 1997, vol. 20, No. 8, pp. 45-53 (Abstract).

Peled, N., et al., Nocturnal ischemic events in patients with obstructive sleep apnea syndrome and ischemic heart disease: effects of continuous positive air pressure treatment, Journal American Coll Cardiology, Nov. 1999, vol. 15, p. 34 (Abstract).

Pelttari, Lisa H., et al., Little Effect of Ordinary Antihypertensive Therapy on Nocturnal High Blood Pressure in Patients with Sleep Disordered Breathing, American Journal of Hypertension, 1998, vol. 11, No. 3, Part 1, pp. 272-279.

Penzel, T., et al., Systematic Comparison of Different Algorithms for Apnoea Detection Based on Electrocardiogram Recordings, Medical & Biological Engineering and Computing 2002, vol. 40, pp. 402-407.

Pepin et al., Does Oximetry contribute to the Detection of Apneic Events? Mathematical. Processing of the $SaO_2$ Signal, Chest, May 1991; 99: 1151-1157.

Peppard, Paul E., et al., Prospective Study of the Association Between Sleep/Disordered Breathing and Hypertension, May 11, 2000, vol. 342, No. 19, pp. 1378-1384.

Peters, John P. Jr., et al., Studies of the Carbon Dioxide Absorption Curve of Human Blood, Book: The Journal of Biological Chemistry, pp. 709-716, Received for publication, Feb. 7, 1923.

Peters, John P. Jr., et al., The Carbon Dioxide Absorption Curve and Carbon Dioxide Tension of the Blood of Normal Resting Individuals, Book: Carbon Dioxide Absorption Curve, pp. 489-547, Received for publication, Dec. 2, 1920 (missing pp. 490, 491, 538-541).

Phillips, Barbara A., et al., Catching Up on Sleep, The National Sleep Disorders Research Plan, Editorial, Chest, vol. 110, No. 5, Nov. 1996, pp. 1132-1133.

Phillips, Susan, et al., Obstructive Sleep Apnoea: Diagnosis and Management, Nursing Standard, vol. 11, No. 17, pp. 43-46, 1997.

Phillipson, Eliot A., Sleep Apnea—A Major Public Health Problem, Editorials, The New England Journal of Medicine, Editorials, vol. 328, No. 17, pp. 1271-1273, Apr. 29, 1993.

Pickett, John, et al.; "Pulse Oximetry and PPG Measurements in Plastic Surgery," Proceedings—19th International Conference—IEEE/EMBS, Chicago, Illinois, Oct. 30-Nov. 2, 1997, pp. 2330-2332.

Plastiras, James, Sleep disorders create need for more sleep labs, Capital District Business Review, Mar. 9, 1998.

Poets, C. F., et al., Arterial oxygen saturation and breathing movements during the first year of life, Journal Developmental Physiology, Jun. 1991, vol. 15, No. 6, pp. 341-345 (Abstract).

Poets, C. F., et al., Home monitoring of transcutaneous oxygen tension in the early detection of hypoxaemia in infants and young children, Arch Dis Child, Jun. 1991, vol. 66, No. 6, pp. 676-682 (Abstract).

Poets, C. F., et al., Oxygen saturation and breathing patterns in infancy. 2: Preterm infants at discharge from special care, Arch Dis Child, May 1991, vol. 66, No. 5, pp. 574-578 (Abstract).

Poets, C. F., et al., Patterns of oxygenation during periodic breathing in preterm infants, Early Human Development, Jul. 1991, vol. 26, No. 1, pp. 1-12 (Abstract).

Poets, C. F., et al., Apparent life/threatening events and sudden infant death on a monitor, Paediatr Respiratory Review, 2004, Suppl. A, pp. S383-S386 (Abstract).

Pradhan, Pratik S., et al., Screening for Obstructive Sleep Apnea in Patients Presenting for Snoring Surgery, Laryngoscope, vol. 106, Nov. 1996, pp. 1393-1397.

Principe/Rodriguez, K., et al., Sleep symptoms and clinical markers of illness in patients with heart failure, Sleep Breath., Sep. 2005, vol. 9, No. 3, pp. 127-133 (Abstract).

Quinn, S. J., et al., The Differentiation of Snoring Mechanisms Using Sound Analysis, Clinical Otolaryngol., 1996, vol. 21, pp. 119-123, Publisher: Blackwell Science Ltd.

Randerath, Winfried J., et al., Autoadjusting CPAP Therapy Based on Impedance Efficacy, Compliance and Acceptance, American Journal Respiratory Critical Care Medicine, vol. 163, pp. 652-657, 2001, Internet address: www.atsjournals.org.

Rapoport, David M., et al., Reversal of the "Pickwickian Syndrome" by Long/Term Use of Nocturnal Nasal/Airway Pressure, The New England Journal of Medicine, Oct. 7, 1982, vol. 307, No. 15, pp. 931-933.

Rapoport, et al., CO2 Homeostasis During Periodic Breathing: Predictions From a Computer Model, The American Journal of Applied Physiological, 1993, vol. 75, Issue 5, pp. 2302-2309.

Rauscher et al., Computerized Detection of Respiratory Events During Sleep from Rapid Increases in Oxyhemoglobin Saturation, Lung, 1991; 169: 355-42.

Rauscher et al., Quantification of sleep/disordered breathing by computerized analysis of oximetry, heart rate, and snoring, Eur Respir J. Jun. 1991; 4: 655-659.

Rauscher, Helmuth, et al., Computerized Detection of Respiratory Events During Sleep from Rapid Increases in Oxyhemoglobin Saturation, Lung, 1991, vol. 169, pp. 335-342.

Redline, Susan, et al., Hypopnea, a Floating Metric: Implications for Prevalence, Morbidity Estimates, and Case Finding, Sleep, vol. 20, No. 12, pp. 1209-1217 (1997).

Redline, Susan, et al., Recognition and Consequences of Obstructive Sleep Apnea Hypopnea Syndrome, Sleep Disorders, Clinics in Chest Medicine, vol. 19, No. 1, Mar. 1998, Cleveland, Ohio, USA (Article and Abstract).

Reite, Martin, et al., The Use of Polysomnography in the Evaluation of Insomnia, An American Sleep Disorders Association Review, Sleep, vol. 18, No. 1, 1995, pp. 58-70, American Sleep Disorders Association and Sleep Research Society 1995.

Remmers, John E., et al., Nasal Airway Positive Pressure in Patients with Occlusive Sleep Apnea, Methods and Feasibility, American Review Respiratory Disorders, Dec. 1984, vol. 130, No. 6, pp. 1152-1155.

Rennotte, M. T., Epidural opioids and respiratory arrests, Anesth Analg., Aug. 1997, vol. 85, No. 2, pp. 452-460 (Abstract).

Resta, O., et al., Sleep/related breathing disorders in acute respiratory failure assisted by non/invasive ventilatory treatment: utility of portable polysomnographic system, Respir Medicine, Feb. 2000, vol. 94, No. 2, pp. 128-134 (Abstract).

Riley, Robert W., et al., Maxillofacial Surgery and Nasal CPAP, A Comparison of Treatment for Obstructive Sleep Apnea Syndrome, Chest, vol. 98, No. 6, Dec. 1990, pp. 1421-1425.

Riley, Robert W., et al., Maxillofacial Surgery and Obstructive Sleep Apnea: A Review of 80 Patients, Otolaryngology—Head and Neck Surgery, vol. 101, No. 3, Sep. 1989, pp. 353-361.

Riley, Robert W., et al., Maxillofacial Surgery and Obstructive Sleep Apnea Syndrome, Otolaryngologic Clinics of North America, vol. 23, No. 4, Aug. 1990, pp. 809-824.

Rosenberg, J., et al., Ventilatory Pattern and Associated Episodic Hypoxaemia in the Late Postoperative Period in the General Surgical Ward, Anaesthesia, 1999, vol. 54, pp. 323-328, Publisher: Blackwell Science Ltd.

Roux, Francoise, et al., Sleep/related Breathing Disorders and Cardiovascular Disease, The American Journal of Medicine, Apr. 1, 2000, vol. 108, pp. 396-400.

Ruchala, Joanna B., Chapter 13, Applications of Pulse Oximetry, Book: Design of Pulse Oximeters, pp. 214-236, 1997.

Ruhle, K. H., et al., Monitoring at Home, Lung, 1990, Suppl, pp. 927-932, Lung, Springer/Verlag, New York, Inc. 1990.

Rundell, O. H., et al., Polysomnography Methods and Interpretations, Sleep Apnea, Otolaryngologic Clinics of North America, vol. 23, No. 4, Aug. 1990, pp. 583-592.

Rusch, T. L., et al., Signal Processing Methods for Pulse Oximetry, Computers in Biology & Medicine, vol. 26, No. 2, pp. 143-159, Mar. 1996 (Abstract).

Ryan, C. Francis, et al., Mechanical Properties of the Velopharynx in Obese Patients with Obstructive Sleep Apnea, American Journal Respiratory Critical Care Medicine, 1996, vol. 154, pp. 806-812.

Ryan, Clodagh M., et al., Periodicity of Obstructive Sleep Apnea in Patients With and Without Heart Failure, Chest 2005; 127, pp. 536-542.

Saarelainen, Seppo, et al., Effect of Nasal CPAP Treatment on Plasma Volume, Aldosterone and 24/h Blood Pressure in Obstructive Sleep Apnoea, Journal Sleep Research, 1996, vol. 5, pp. 181-185.

Sadeh, Avi, et al., The Role of Actigraphy in the Evaluation of Sleep Disorders, An American Sleep Disorders Association and Sleep Research Society, Sleep, vol. 18, No. 4, pp. 288-302, 2002.

Sadrmoori, Bijan, Evaluation of Self Adjusting Nasal CPAP (DPAP) in the Treatment of Adult Obstructive Sleep Apnea, Sleep Research No. 23, 1994, p. 386 (Abstract).

Saito, Toshiyuki, et al., Sleep Apnea in Patients with Acute Myocardial Infarction, Critical Care Medicine, vol. 19, No. 7, pp. 938-941, Printed in USA, Copyright 1991 by Williams and Wilkins.

Sajkov, Dimitar, et al., Daytime Pulmonary Hemodynamics in Patients with Obstructive Sleep Apnea without Lung Disease, American Journal Respiratory Critical Care Medicine, 1999, vol. 159, pp. 1518-1526.

Salmi, et al., Evaluation of Automatic Analysis of SCSB, Airflow and Oxygen Saturation Signals in Patients with Sleep Related Apneas, Chest, 1989; 96: 255-61.

Sanders, Mark H., et al., Obstructive Sleep Apnea Treated by Independently Adjusted Inspiratory and Expiratory Positive Airway Pressures via Nasal Mask, Physiologic and Clinical Implications, Chest, vol. 98, No. 2, Aug. 1990, pp. 317-324.

Sanders, Mark H., Nasal CPAP Effect on Patterns of Sleep Apnea, Chest, vol. 86, No. 6, Dec. 1984, pp. 839-844.

Sangal, R. Bart et al., P300 Latency: Abnormal in Sleep Apnea with Somnolence and Idiopathic Hypersomnia, but Normal in Narcolepsy, Clinical Electroencephalography, 1995, vol. 26, No. 3, pp. 146-153, Troy, Michigan, USA.

Sanna, A., et al., Apport de la Polysomnographie à la mise au point des maladies atteints d'une bronchopneumopathie chronique obstructive (BPCO), Travail Original, Rev. Mèd. Brux., vol. 12, pp. 315-320, 1991, Belgium.

Sanner, B. M., et al., Sleep/related respiration disorders: their relevance in intensive care medicine, [Article in German], Dtsch Med Wochenschr, Mar. 1999, vol. 12, p. 124 (Abstract).

Sarodia, B.D. et al. Prevalence of obstructive sleep apnea in patients admitted to the intensive care unit with cardiovascular events, Sleep Research, 1996, vol. 25, pp. 356.

Schafer, H., et al., Cardiovascular morbidity in patients with obstructive sleep apnea in relation to the severity of respiratory disorder, Dtsch Med Wochenschr, 1998, vol. 123, No. 39, pp. 1127-1133 (Abstract).

Schafer, H., et al., Pulmonary Haemodynamics in Obstructive Sleep Apnoea: Time Course and Associated Factors, European Respiratory Journal, 1998, vol. 12, pp. 679-684, Printed in United Kingdom.

Schagatay, E., et al., Diving Response and Apneic Time in Humans, Undersea Hyper Med., 1998, vol. 25, No. 1, pp. 13-19, Copyright 1988 Underseas and Hyperbaric Medical Society, Inc.

Scharf, Martin B., et al., Cyclic Alternating Pattern Sequences in Non/Apneic Snorers With and Without Nasal Dilation, ENT/Ear, Nose & Throat Journal, Sep. 1996, vol. 75, No. 9, pp. 617-619.

Scharf, Steven M., et al., Cardiovascular Effects of Periodic Occlusions of the Upper Airways in Dogs, American Review of Respiratory Disease, pp. 321-329, 1992.

Scheers, N. J., et al., Sudden Infant Death With External Airways Covered, Case/Comparison Study of 206 Deaths in the United States, Arch Pediatric Adolescent Medicine, 1998, vol. 152, pp. 540-547.

Schmidt/Notwara, Wolfgang, et al., Oral Appliances for the Treatment of Snoring and Obstructive Sleep Apnea: A Review, An American Sleep Disorders Association Review, Sleep, vol. 18, No. 6, pp. 501-510, 1995, American Sleep Disorders Association and Sleep Research Society.

Schnader, Jeff, Increase of Pulmonary Artery Occlusion Pressure During Upper Airway Obstruction in Sleep Apnea, Case Reports, Critical Care Medicine, 1996, vol. 24, No. 2, pp. 354-358.

Schnapp, Lynn M., et al., Pulse Oximetry Uses and Abuses, Critical Care, Chest, vol. 98, No. 5, Nov. 1990, pp. 1244-1250.

Schneider, H., et al., Neural and local effects of hypoxia on cardiovascular responses to obstructive apnea, Journal Appl Physiol., Mar. 2000, vol. 88, No. 3, pp. 1093-1092 (Abstract).

Schoenberg, R., et al., Making ICU Alarms Meaningful: A Comparison of Traditional vs. Trend/Based Algorithms, AMIA 1999, Annual Symposium (Abstract).

Schwab, Richard J., et al., Upper Airway and Soft Tissue Structural Changes Induced by CPAP in Normal Subjects, American Journal Respiratory Critical Care Medicine, 1996, vol. 154, pp. 1106-1116.

Seelbach-Göbel, Birgit, et al.; "The prediction of fetal acidosis by means of intrapartum fetal pulse oximetry," Am J. Obstet. Gynecol., vol. 180, No. 1, Part 1, pp. 73-81 (1999).

Senn, Oliver et al., Monitoring Carbon Dioxide Tension and Arterial Oxygen Saturation by a Single Earlobe Sensor in Patients With Critical Illness or Sleep Apnea, Chest 2005, vol. 128, pp. 1291-1296, Northbrook, IL, USA.

Series et al., Utility of Nocturnal Home Oximetry for Case Finding in Patients with Suspected Sleep apnea Hypopnea Syndrome, Sep. 15, 1993, Annals of Internal Medicine, col. 119, p. 449-453.

Series, et al., Influence of Continuous Positive Airways Pressure on Sleep Apnea/Related Desaturation in Sleep Apnea Patients, Lung, 1992; 170: 281-290.

Series, Frederic, et al., Prospective Evaluation of Nocturnal Oximetry for Detection of Sleep/Related Breathing Disturbances in Patients With Chronic Heart Failure, Chest 2005, vol. 127, pp. 1507-1514, Northbrook, IL, USA.

Severinghaus, John W., et al., Recent Developments in Pulse Oximetry, Anesthesiology, vol. 76, pp. 1018-1038, 1992.

Shamir, M. et al., Pulse oximetry plethsymographic waveform during changes in blood volume, British Journal of Anaesthesia, vol. 82(2), pp. 178-181, 1999, Great Britain.

Shepard, J., Gas Exchange and Hemodynamics During Sleep, Medical Clinics of North America, vol.. 69, No. 6, Nov. 1985, pp. 1243-1265.

Shephard, John W. Jr., et al., Relationship of Ventricular Ectopy to Oxyhemoglobin Desaturation in Patients with Obstructive Sleep Apnea, Chest, vol. 88, No. 3, Sep. 1985, pp. 335-340, Northbrook, IL, USA.

Shephard, John W., Jr., et al., Uvulopalatopharyngoplasty for Treatment of Obstructive Sleep Apnea, Mayo Clinic Proceedings, vol. 65, pp. 1260-1267, 1990.

Sher, Aaron E., et al., The Efficacy of Surgical Modifications of the Upper Airway in Adults With Obstructive Sleep Apnea Syndrome, An American Sleep Disorders Association Review, Sleep, vol. 19, No. 2, pp. 156-177, Nov. 1995.

Shinohara, E., et al., Visceral Fat Accumulation as an Important Risk Factor for Obstructive Sleep Apnoea Syndrome in Obese Subjects, Journal of Internal Medicine, vol. 241, pp. 11-18, Publisher: Blackwell Science Ltd., 1997.

Shoemaker, W. C. et al., Incidence, Physiologic Description, Compensatory Mechanisms, and Therapeutic Implications of Monitored Events, Critical Care Medicine, Dec. 1989, vol. 17, No. 12, pp. 1277-1285.

Shoemaker, W. C. et al., Multicenter study of noninvasive monitoring systems as alternatives to invasive monitoring of acutely ill emergency patients, Chest, 1998; vol. 114; pp. 1643-1652.

Shoemaker, W. C. et al., Noninvasive Physiologic Monitoring of High/Risk Surgical Patients, Archives of Surgery, vol. 131, No. 7, Jul. 1996, pp. 732-737.

Shoemaker, W. C. et al., Prediction of Outcome and Severity of Illness by Analysis of the Frequency Distributions of Cardiorespiratory Variables, Critical Care Medicine, vol. 5, No. 2, Mar./Apr. 1977, pp. 82-88.

Shoemaker, W. C. et al., Sequence of Physiologic Patterns in Surgical Septic Shock, Critical Care Medicine, Dec. 21, 1993 (12): pp. 1821.

Shoemaker, W. C., Cardiorespiratory Patterns in Complicated and Uncomplicated Septic Shock: Physiologic Alterations and Their Therapeutic Implications, Ann. Surg., Jul. 1971, vol. 174, No. 1, pp. 119-125.

Shoemaker, W. C., Early Physiologic Patterns in Acurate Illness and Accidents: Toward a Concept of Circulatory Dysfunction and Shock Based on Invasive and Noninvasive Hemodynamic Monitoring, New Horizons, Nov. 1996, vol. 4, No. 4, pp. 395-412.

Shoemaker, W. C., Temporal Physiologic Patterns of Shock and Circulatory Dysfunction Based on Early Descriptions by Invasive and Noninvasive Monitoring, New Horizons, vol. 4, No. 2, May 1996, pp. 300-318.

Shoemaker, W.C., Oxygen Transport and Oxygen Metabolism in Shock and Critical Illness, Invasive and Noninvasive Monitoring of Circulatory Dysfunction and Shock, Critical Care Clinics, vol. 12, No. 4, Oct. 1996, pp. 939-969.

Siggaard/Andersen O. et al.; *The Bohr Effect and the Haldane Effect*; Scand J Clin Lab Invest; vol. 3 (1); 1973; pp. 1-8.

Silverberg, D. S., et al., Essential and Secondary Hypertension and Sleep/Disordered Breathing: A Unifying Hypothesis, Journal of Human Hypertension, 1996, vol. 10, pp. 353-363.

Silverberg, D., et al., Sleep apnoea and hypertension. Active approach to detection of obstructive sleep apnoea is imperative, BMJ, Jul. 2000, vol. 22, pp. 321 (Abstract).

Silverberg, Donald, The Joint National Committee on Prevention, Detection, Evaluation, and Treatment of High Blood Pressure and Obstructive Sleep Apnea: Let Their Silence Not Be Matched by the Silence of the Ordinary Physician, Arch Intern Med., Jun. 8, 1998, vol. 158, pp. 1272-1273.

Simmons, Richard L. et al.; *The Role of the Central Nervous System in Septic Shock: II. Hemodynamic, Respiratory and Metabolic Effects of Intracisternal or Intraventricular Endotoxin*; Annals of Surgery; Feb. 1968; pp. 158-167.

Sin, D. D., et al., Effects of continuous positive airway pressure on cardiovascular outcomes in heart failure patients with and without Cheyne/Stokes respiration, Circulation, Jul. 2000, vol. 102, No. 1, pp. 61-66 (Abstract).

Sinex, James E.; *Pulse Oximetry: Principles and Limitations*; American Journal of Emergency Medicine; vol. 17, No. 1; Jan. 1999; pp. 59-66.

Skjodt, N. M., et al., Screening for hypothyroidism in sleep apnea, American Journal of Respiratory & Critical Care Medicine, vol. 160, No. 2, pp. 732-735, Aug. 1999 (Abstract).

Slutsky et al., Quantification of Oxygen Saturation During Episodic Hypoxemia, American Review of Respiratory Disease, 1980; 121:893-895.

Smith, Philip E. M., et al., Hypoxemia During Sleep in Duchenne Muscular Dystrophy, American Review Respiratory Disorders, 1988, vol. 137, pp. 884-888.

Smyth, Edward, et al., Apneic Oxygenation Associated with Patient/Controlled Analgesia, Journal of Clinical Anesthesia, vol. 10, pp. 499-501, 1998, Publisher: Elsevier Science, Inc., New York, NY, USA.

Soto, F. Cardiovascular manifestations of obstructive sleep apnea. Effects of the treatment, Rev Med Chil., [Article in Spanish], Sep. 1998, vol. 126, No. 9, pp. 1112-1116 (Abstract) i.

Soubani, Ayman O.; *Noninvasive Monitoring of Oxygen and Carbon Dioxide*; American Journal of Emergency Medicine; vol. 19, No. 2; Mar. 2001; pp. 141-146.

Spector, Rosanne, Low/tech Screening for high/risk breathing disorder, http://healthlink.stanford.edu/healthlink/news2/lowtech.thml, Copyright 1996 Stanford University Medical Center News Bureau.

Spigulis, Janis, et al.; "Optical multi-channel sensing of skin blood pulsations," Optical Sensing, Proceedings of SPIE, vol. 5459, pp. 46-53 (2004).

Staniforth, A. D., et al., Nocturnal desaturation in patients with stable heart failure, Heart, Apr. 1998, vol. 79, No. 4, pp. 394-399, United Kingdom.

Stebbens, V. A., Oxygen saturation and breathing patterns in infancy. 1: Full term infants in the second month of life, Arch Dis Child, May 1991, vol. 66, No. 5, pp. 569-573 (Abstract).

Stegman, S. S., et al., Asymptomatic bradyarrhythmias as a marker for sleep apnea: appropriate recognition and treatment may reduce the need for pacemaker therapy, Pacing Clin Electrophysiol, Jun. 1996, vol. 19, No. 6, pp. 899-904 (Abstract).

Stradling, J. R., et al., Automatic Nasal Continuous Positive Airway Pressure Titration in the Laboratory: Patient Outcomes, Thorax, 1997, vol. 52, pp. 72-75.

Stradling, J. R., et al., Predictors and Prevalence of Obstructive Sleep Apnoea and Snoring in 1001 Middle Aged Men, Thorax, 1991, vol. 46, pp. 85-90.

Stradling, John R., et al., Relation between systemic hypertension and sleep hypoxaemia or snoring: analysis in 748 men drawn from general practice, BMJ, vol. 300, Jan. 13, 1990, pp. 75-78.

Strohl et al., Oxygen Saturation During Breath Holding and During Apneas in Sleep, Chest, Feb. 1984: 85, No. 1; 181-186.

Strohl, Kingman P., Consequences of Sleep/Disordered Breathing, Respiratory Care, Apr. 1998, vol. 43, No. 4, pp. 277-282.

Strohl, Kingman P., et al., Physiologic Basis of Therapy for Sleep Apnea, State of Art: Physiologic Basis of Therapy for Sleep Apnea, pp. 791-802, 2007.

Sullivan, Colin E., et al., Reversal of Obstructive Sleep Apnoea by Continuous Positive Airway Pressure applied through the Nares, The Lancet, Apr. 18, 1981, pp. 862, 865.

Sullivan, Mary Anna et al., PCA Update, Unexpected Deaths of Patients Receiving Patient/Controlled Analgesia, Nov. 2001.

Svanborg, et al., A Limited diagnostic Investigation for Obstructive Sleep Apnea Syndrome: Oximetry and Static Charge Sensitive Bed, Chest, 1990; 98: 1341-1345.

Svatikova, A., et al., Plasma brain natriuretic peptide in obstructive sleep apnea, American Journal Cardiology, Aug. 15, 2004, vol. 94, No. 4, pp. 529-532 (Abstract).

Szaboova, E., et al., Obstructive Sleep Apnea as a Cause of Dysrhythmia in Sudden Cardiac Death, Bratisl Lek Listy, Jul./Aug. 1997, vol. 98, No. 7-8, pp. 448-453 (Abstract).

Tan and T. H. Koh, Evaluation of Obstructive Sleep Apnea in Singapore Using Computerized Polygraphic Monitoring, Annals Academy of Medicine, Mar. 1991, vol. 20 No. 2, pp. 196-200.

Tanchaiswad, Waran, Is Sudden Unexplained Nocturnal Death a Breathing Disorder?, Review Article, Psychiatry and Clinical Neurosciences, 1995, vol. 49, pp. 111-114.

Tang, et al.; *Perepheral neural modulation of endotoxin/induced hyperventilation*; Critical Care Medicine; vol. 26, Issue 9; Sep. 1998, pp. 1558-1563.

Tanigawa, T., et al., Screening for sleep/disordered breathing at workplaces, Ind. Health, Jan. 2005, vol. 43, No. 1, pp. 53-57 (Abstract).

Tatevossian, Raymond G., et al., Noninvasive Hemodynamic Monitoring for Early Warning of Adult Respiratory Distress Syndrome in Trauma Patients, Journal of Critical Care, vol. 15, No. 4 (December), 2000, pp. 151-159.

Tatevossian, Raymond G., et al., Transcutaneous oxygen and C02 as early warning of tissue hypoxia and hemodynamic shock in critically ill emergency patients ; *Critical Care Med.*; vol. 28, No. 7; pp. 2248-2253 (2000).

Teramoto, S., et al., Does the altered cardiovascular variability associated with obstructive sleep apnea contribute to development of cardiovascular disease in patients with obstructive sleep apnea syndrome?, Circulation, Dec. 21, 1999, vol. 100, No. 25, pp. e136-e137 (Abstract).

Teschler, H., et al., Influence of Moderate Alcohol Consumption on Obstructive Sleep Apnoea with and without AutoSet™ Nasal CPAP Therapy, European Respiratory Journal, 1996, vol. 9, pp. 2371-2377, Printed in United Kingdom.

Teschler, Helmut, et al., Automated Continuous Positive Airway Pressure Titration for Obstructive Sleep Apnea Syndrome, American Journal Respiratory Critical Care Medicine, vol. 154, pp. 734-740, 1996.

The American Sleep Disorders Association Accreditation Committee, Standards for Accreditation of Sleep Disorders Centers, American Sleep Disorders Association, Rochester, MN, Mar. 1997, Revised Edition, pp. 1-17 (p. 16 missing).

Thorpy, Michael J., The Clinical Use of the Multiple Sleep Latency Test, Report From the American sleep Disorders Association, Sleep, vol. 15, No. 3, 1992, pp. 268-276, American Sleep Disorders Association and Sleep Research Society.

Thorpy, Michael, et al., ASDA Standards of Practice, Practice Parameters for the Use of Portable Recording in the Assessment of Obstructive Sleep Apnea, Standards of Practice Committee of the American Sleep Disorders Associate, Sleep, vol. 17, No. 4, pp. 372-377 (1994).

Thorpy, Michael, et al., Practice Parameters for the Treatment of Obstructive Sleep Apnea in Adults: The Efficacy of Surgical Modifications of the Upper Airway, An American Sleep Disorders Association Review, Sleep, vol. 19, No. 2, pp. 152-155, 1996, American Sleep Disorders Association and Sleep Research Society.

Thorpy, Michael, et al., Practice Parameters for the Treatment of Snoring and Obstructive Sleep Apnea with Oral Appliances, An American Sleep Disorders Association and Sleep Research Society, Sleep, vol. 18, No. 6, pp. 511-513, 1995.

Thorpy, Michael, et al., Practice Parameters for the Use of Actigraphy in the Clinical Assessment of Sleep Disorders, An American Sleep Disorders Association Report, Sleep, vol. 18, No. 4, pp. 285-287, 1995 American Sleep Disorders Association and Sleep Research Society.

Thorpy, Michael, et al., Practice Parameters for the Use of Laser/assisted Uvulopalatoplasty, An American Sleep Disorders Association and Sleep Research Society, Sleep, vol. 17, No. 8, pp. 744-748, 1994.

Thorpy, Michael, et al., Practice Parameters for the Use of Polysomnography in the Evaluation of Insomnia, An American Sleep Disorders Association Report, Sleep, vol. 18, No. 1, pp. 55-57, 1995 American Sleep Disorders Association and Sleep Research Society.

Timms et al., Oxygen Saturation by Oximetry: analysis by Microcomputer, Journal of Polysomographic Technology, Spring 1988: 13-21.

Timms, et al., and Profox Associates, Inc., Profox for the Bedside, Version 8SP Nov. 1992, Programs for Oximetry [IBM], User's Manual, Nov. 1992, 20 total pages.

Tkacova, R., et al., Continuous positive airway pressure improves nocturnal barareflex sensitivity of patients with heart failure and obstructive sleep apnea., Journal Hypertension, Sep. 2000, vol. 18, No. 9, pp. 1257-1262 (Abstract).

Tkacova, R., et al., Effects of continuous positive airway pressure on obstructive sleep apnea and left ventricular afterload in patients with heart failure, Circulation, 1998, vol., 98, No. 21, pp. 2269-2275 (Abstract).

Tobert, Daren G., et al., Laboratory Medicine and Pathology, New Directions for Pulse Oximetry in Sleep Disorders, Mayo Clinic Proceedings, 1995, vol. 70, pp. 591, Rochester, Minnesota, USA.

Tobin, Martin J., et al., Breathing Abnormalities During Sleep, Arch Intern Med, vol. 143, Jun. 1983, pp. 1221-1228.

Trang, H., et al., [B20] [Poster: 904] Masimo SetR Pulse Oximetry Improves Detection of Sleep Apnea/Related Hypoxemia, Nov. 2, 2001, C:/Masimo/Biblio, p. 1 of 1.

Tremel, F., et al., High prevalence and persistence of sleep apnoea in patients referred for acute left ventricular failure and medically treated over 2 months, European Heart Journal, Aug. 1999, vol. 20, No. 16, pp. 120-129.

Trinder, J., et al., Pathophysiological interactions of ventilation, arousals, and blood pressure oscillations during Cheyne/Stokes respiration in patients with heart failure, American Journal Respiratory Critical Care Medicine, Sep. 2000, vol. 162, No. 3 Pt. 1, pp. 808-813 (Abstract).

Trupp, R. J., et al., Prevalence of sleep disordered breathing in a heart failure program, Congestive Heart Failure, Sep./Oct. 2004, vol. 10, No. 5, pp. 217-220 (Abstract).

Trupp, R. J., The heart of sleep: sleep/disordered breathing and heart failure, Journal Cardiovascular Nursing, Nov./Dec. 2004, vol. 19, No. 6 Suppl, S67-74 (Abstract).

Ullmer, E., et al., Cheyne/stokes respiration or obstructive sleep apnoea: patterns of desaturation, Respiration, 2000, vol. 67, No. 2, p. 203 (Abstract).

VanBoxem, T. J., et al., Prevalence and severity of sleep disordered breathing in a group of morbidly obese patients, Netherlands Journal of Medicine, vol. 54, No. 5, pp. 202-206, May 1999 (Abstract).

VanSlyke, Donald D., et al., Studies of Gas and Electrolyte Equilibria in Blood, pp. 781-798, Journal Biol. Chem., Oct. 1928, vol. 79, No. 2.

Våzquez, Juan/Carlos, et al.; "Automated Analysis of Digital Oximetry in the Diagnosis of Obstructive Sleep Apnoea,"; *Thorax*, vol. 55, pp. 302-307; 2000.

Verbraecken, J., et al., Chronic $CO_2$ Drive in Patients with Obstructive Sleep Apnea and Effect of CPAP, Respiration Physiology, vol. 101, pp. 279-287, 1995, Publisher: Elsevier.

Vgontzas, Alexandros N., et al., Obesity Without Sleep Apnea is Associated with Daytime Sleepiness, Arch Intern Med., Jun. 22, 1998, vol. 158, pp. 1333-1337.

Vidhani, K., et al., Obstructive sleep apnoea syndrome: is this an overlooked cause of desaturation in the immediate postoperative period?, British Journal Anaesth, Apr. 1997, vol. 78, No. 4, pp. 442-443 (Abstract).

Visser, B.F., Pulmonary Diffusion of Carbon Dioxide, Med. Biol. vol. 5, pp. 155-166, Issue 2, Oct. 1960.

Waldhorn, Richard E., Surgical Treatment of Obstructive Sleep Apnea, is Mandibular Surgery an Advance?, Chest, 1998, vol. 6, Dec. 1990, pp. 1315-1316.

Walker, Regina Paloyan, et al., Uvulopalatopharyngoplasty Versus Laser/Assisted Uvulopalatoplasty for the Treatment of Obstructive Sleep Apnea, Laryngooscope, vol. 107, Jan. 1997, pp. 76-82.

Weber, W., et al., Low/Perfusion Resistant Pulse Oximetry, Abstract Only, Journal of Clinical Monitoring, vol. II, No. 4, Jul. 1995, p. 284.

Weiss, et al., "Computer Assisted Physiologic Monitoring and Stability Assessment in Vascular Surgical Patients Undergoing General Anesthesia—Preliminary Data," Journal of Clinical Monitoring and Computing, 16:107-113, 2000.

Weiss, J. Woodrow, et al., Cardiovascular Morbidity in Obstructive Sleep Apnea, Progress in Cardiovascular Diseases, vol. 41, No. 5, Mar./Apr. 1999, pp. 367-376.

Wessendorft, T. E., et al., Sleep/disordered breathing among patients with first/ever stroke, Journal Neurology, Jan. 2000, vol. 247, No. 1, pp. 41-47 (Abstract only).

West, Peter, et al., Dynamic in Vivo Response Characteristics of Three Oximeters: Hewlett/Packard 47201A, Biox II, and Nellcor N/100, Sleep, vol. 10, No. 3, 1987, pp. 263-271, Raven Press, New York, USA.

Westesson, Per/Lennart, et al., Morbidity after temporomandibular joint arthrography is lower than after removal of lower third molars, Oral Surgery Oral Medical Oral Pathol., 1990, vol. 70, pp. 2-4.

Wheatley, J. R., et al., Mechanical properties of the upper airway, Curr Opin Pulm Medicine, Nov. 1998, vol. 4, No. 6, pp. 363-369 (Abstract).

White, D. P., et al., Assessment of Accuracy and Analysis Time of a Novel Device to Monitor Sleep and Breathing in the Home, Sleep, vol. 18, No. 2, Feb. 1995, pp. 115-126.

White, David P., Pathophysiology of Obstructive Sleep Apnoea, Sleep/Related Breathing Disorder—2, Thorax, 1995, vol. 50, pp. 797-804.

Whitelaw, William A., et al., Clinical Usefulness of Home Oximetry Compared with Polysomnography for Assessment of Sleep Apnea, American Journal Respiratory Critical Care Medicine, vol. 171, pp. 188-193, 2005, Internet address: www.atsjournals.org.

Whitman, R. A., et al., Comparison of the New Masimo SET V3 Technology with a Conventional Pulse Oximeter during Polysomnography, Sleep, 2001, vol. 24, pp. A412 (730.R).

Wiater, A., et al., Polysomnographic Standards for Infants and Children, Somnologie, vol. 4, pp. 39-42, 2000, Berlin—Wien.

Wieczorek, Paul M., et al., Obstructive Sleep Apnea Uncovered After High Spiral Anesthesia: A Case Report, Cardiothoracic Anesthesia, Respiration and Airway, Canadian Journal of Anesthesia, 2005, vol. 52, No. 7, pp. 761-764.

Wilhoit, Stephen C., et al., Comparison of Indices Used to Detect Hypoventilation during Sleep, Respiration, vol. 47, pp. 237-242, 1985.

Wilkins, Robert L., et al., Egan'S Fundamentals of Respiratory Care, Analysis and Monitoring of Gas Exchange, Book, Eighth Edition, Chapter 16, Section III, Capnography/Capnometry During Mechanical Ventilation, pp. 383-389, 2008.

Wilkinson, M. H., et al., Effect of Venous Oxygenation on Arterial Desaturation Rate During Repetitive Apneas in Lambs, Respiration Physiology 101 (19950 321-331.

Williams, Adrian J., et al., Clinical Value of Polysomnography, The Lancet, vol. 339, May 2, 1992, p. 1113.

Williams, et al., Screening for Sleep Apnea Using Pulse Oximetry and a Clinical Score, Chest, 100-3, Sep. 1991; pp. 631-635.

Wright, John, et al., Health effects of obstructive sleep apnoea and the effectiveness of continuous positive airways pressure: a systematic review of the research evidence, BMJ, vol. 314, Mar. 22, 1997, pp. 851-860.

Wright, John, et al., Letters, Obstructive Sleep Apnoea, Authors' reply, bmj.com, Jun. 26, 2001.

Wynne, James W., et al., Disordered Breathing and Oxygen Desaturation During Sleep in Patients with Chronic Obstructive Lung Disease (COLD), The American Journal of Medicine, vol. 66, Apr. 1979, pp. 573-579.

Yamakage, M., et al., Changes in respiratory pattern and arterial blood gases during sedation with propofol or midazolam in spinal anesthesia, Journal Clinical Anesth, Aug. 1999, vol. 11, No. 5, pp. 375-379 (Abstract).

Yantis, M. A., Decreasing surgical risks for patients with obstructive sleep apnea, AORN Journal, Jul. 1998, vol. 68, No. 1, pp. 50-55 (Abstract).

Yoon, Gilwon, et al.; Multiple diagnosis based on Photoplethysmography: hematocrit, SpO2, pulse and respiration, Optics in Health Care and Biomedical optics: Diagnostics and Treatment; Proceedings of the SPIE, vol. 4916; pp. 185-188 (2002).

Younes, Magdy, et al. Chemical Control Stability in Patients with Obstructive Sleep Apnea, American Journal Respiratory Critical Care Medicine, vol. 163, pp. 1181-1190, 2001.

Young, Terry, et al., The Gender Bias in Sleep Apnea Diagnosis, Are Women Missed Because They Have Different Symptoms?, Original Investigation, Arch Intern Medicine, vol. 156, Nov. 25, 1996, pp. 2445-2451.

Zafar, Subooha, et al., Choice of Oximeter Affects Apnea/Hypopnea Index, Chest, vol. 127/1, Jan., 2005, pp. 80-88, Clinical Investigations, www.chestjournal.org.

Zamarron, C. et al., Oximetry Spectral Analysis in the Diagnosis of Obstructive Sleep Apnoea, Clinical Science, 1999, vol. 97, pp. 467-473, Printed in Great Britain.

Zoccali, Carmine, et al., Nocturnal Hypoxemia, Night/Day Arterial Pressure Changes and Left Ventricular Geometry in Dialysis Patients, Kidney International, vol. 53, 1998, pp. 1078-1084, International Society of Nephrology.

Zucconi, M., et al., An unattended device for sleep/related breathing disorders: validation study in suspected obstructive sleep apnoea syndrome, European Respiratory Journal, 1996, vol. 9, pp. 1251-1256, Printed in United Kingdom.

Zou, Ding, et al., Obstructive Apneic Events Induce Alpha/Receptor Mediated Digital Vasoconstriction, Sleep, vol. 27, No. 3, 2004, pp. 485-489.

* cited by examiner

SYSTEM AND METHOD FOR EVALUATING PHYSIOLOGICAL PARAMETER DATA

RELATED APPLICATIONS

This application claims priority to U.S. Provisional Application No 61/066,181, filed Feb. 19, 2008, and is incorporated herein by reference in its entirety.

BACKGROUND

Embodiments of the present disclosure may relate to a system and method for evaluating physiological parameter data. In embodiments, a medical device may be capable of calculating an airway instability index from pulse oximetry measurements and generating a smoothed index representing airway instability.

This section is intended to introduce the reader to various aspects of art that may be related to various aspects of the present disclosure, which are described and/or claimed below. This discussion is believed to be helpful in providing the reader with information to facilitate a better understanding of the various aspects of the present disclosure. Accordingly, it should be understood that these statements are to be read in this light, and not as admissions of prior art.

Obstructive sleep apnea is a condition in which a patient's breathing is temporarily interrupted when sleeping. The condition is believed to be associated with increased fat deposits in the neck, which commonly occur as a patient ages. These increased fat deposits may lead to a narrowing of the airway. When muscle tone diminishes during sleep, the narrowed airway can collapse during inhalation, effectively stopping and/or severely limiting air movement. At this point, the choking patient typically attempts to inhale more deeply, which generally results in further collapsing the airway. With no air movement, the oxygen level in the patient's bloodstream falls, finally reaching a point where the patient is aroused out of sleep. Upon arousal, the muscle tone increases, the airway opens and air flow to the lungs is precipitously restored. The patient hyperventilates, which quickly restores the blood oxygen levels to normal levels. The period of arousal is brief, so the patient is often unaware that the event took place. The patient returns to sleeping and the cycle often repeats.

Over time, this repeating cycle of low oxygen levels in the bloodstream can damage the heart and lead to other serious medical complications. Obstructive sleep apnea is believed to be one of the most common disorders in the United States and an important cause of heart attack and stroke. However, unlike other common medical disorders, such as diabetes, no simple diagnostic test has been developed to determine if a patient has sleep apnea. Tests do exist that can be used to diagnose sleep apnea, but the tests typically involve an overnight sleep study, which can be costly and inconvenient. The need for a simple, low-cost diagnostic test has led medical personnel to try less expensive techniques, such as pulse oximetry, to diagnose the presence of obstructive sleep apnea.

SUMMARY

Certain aspects of embodiments of this disclosure are set forth below. It should be understood that these aspects are presented merely to provide the reader with a brief summary of certain forms the disclosure might take and that these aspects are not intended to limit the scope of the disclosure. Indeed, the disclosure may encompass a variety of aspects that may not be set forth below.

Embodiments may include a method of evaluating physiological parameter data. The method may include monitoring a patient to produce a signal including a sequence of numerical values for a physiological parameter over a time period and calculating an index from the signal. The index may be compared to a reported index and if the index is greater than the reported index, the reported index may be set to the value of the index. A modulation of the signal may be calculated and compared to a previous value of the modulation to identify a trend in the modulation. If the trend corresponds to an undesirable condition, a first function may be used to increase the reported index. The reported index may be used to provide an indication of a physiological status.

Embodiments may include a medical device including a sensor, a microprocessor, a memory, and a display. The sensor may be configured to produce a signal including a sequence of numerical values for a physiological parameter over a time period and the microprocessor may be configured to process the signal. The memory may be configured for storing programs and the contents of the memory may include machine readable instructions configured to direct the microprocessor to obtain the signal from the sensor and calculate an index from the signal. The instructions may, if executed, direct the microprocessor to compare the index to a reported index and if the index is greater than the reported index, set the reported index to the value of the index. The instructions may also direct the microprocessor to calculate a modulation of the signal and compare the modulation to a previous value of the modulation to identify a trend in the modulation. If the trend corresponds to an undesirable condition, the machine readable instructions may direct the microprocessor to increase the reported index using a first function. Finally, the memory may include instructions to direct the microprocessor to provide an indication of a physiological status based on the reported index.

Embodiments may include a tangible, machine readable medium that may include code which, if executed, may cause a microprocessor to obtain a signal made up of a sequence of numerical values for a physiological parameter over a time period and calculate an index from the signal. The tangible, machine readable medium may additionally include code that compares the index to a reported index and if the index is greater than the reported index, set the reported index to the value of the index, and code to calculate a modulation of the signal and compare the modulation to a previous value of the modulation to identify a trend in the modulation. If the trend corresponds to an undesirable condition, the code may increase the reported index using a first function. Finally, the tangible machine-readable medium may include code to provide an indication of a physiological status based on the reported index.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Medical devices may be used to obtain signals representing physiological parameters from patients. However, these signals, which may be sequences of numerical values over time, may have too much information or noise to be effectively used in the diagnosis or treatment of certain medical conditions. Accordingly, the signals may be processed to generate a secondary series of numerical values over time, termed an index, which may provide a more useful representation of the status of the medical condition. In some applications, the index itself may be too responsive to noise or other factors to be easily analyzed. Embodiments may include methods that may be useful for processing an index calculated from a signal to generate a reported index having a decreased response to noise and other clinically insignificant events.

Thus, methods may assist in identifying problematic physiological conditions, while reducing the incidence of nuisance alarms. For example, in an embodiment, a method may increase the effectiveness of the use of oxygen saturation levels obtained from pulse oximetry in the diagnosis and treatment of sleep apnea. However, one of ordinary skill in the art will recognize that the method described below is not limited to pulse oximetry and may be implemented on other systems to calculate indices reflective of other physiological conditions. Examples of such indices may include indices reflective of heart rate variability, brain activity, glucose levels, and other measurements.

Figure 1:
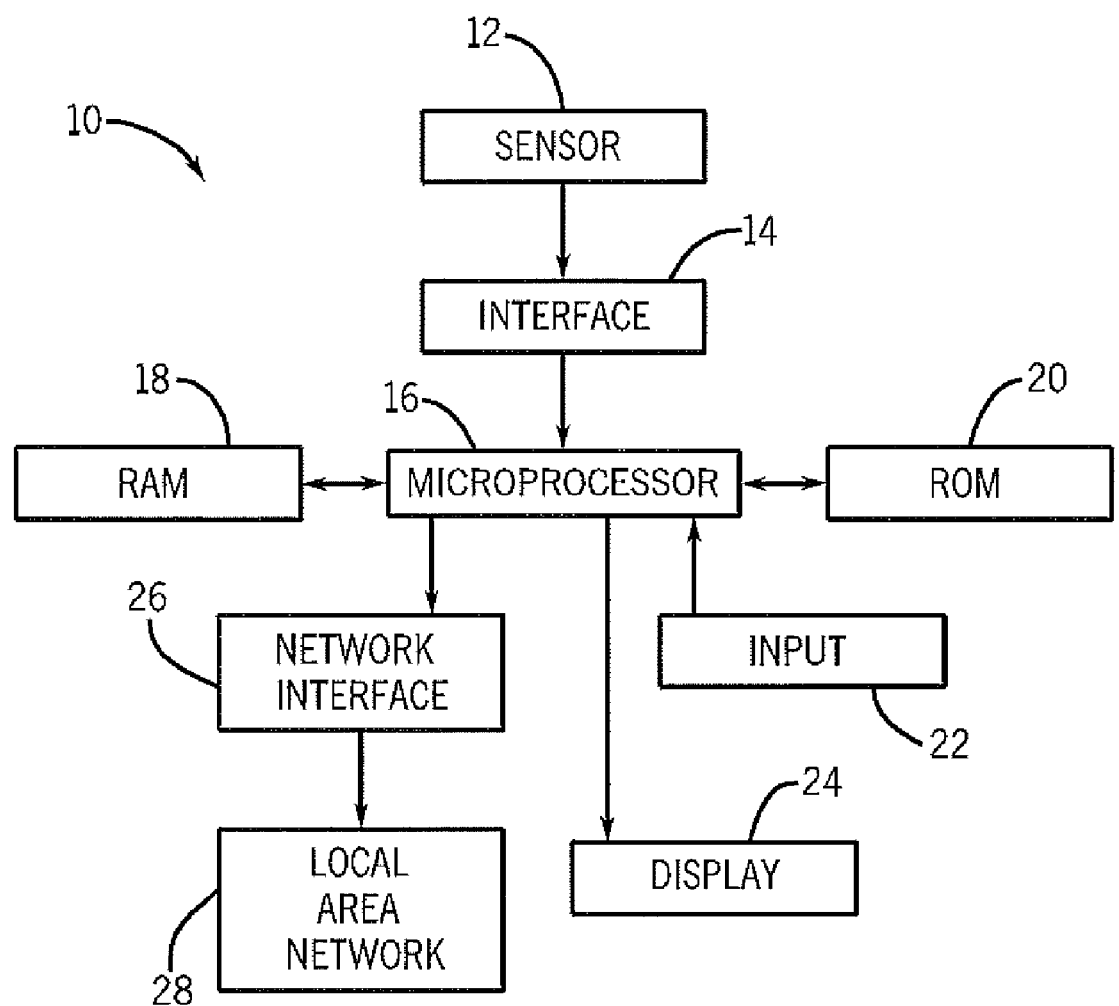
FIG. 1 is a block diagram of a system for the collection of a physiological parameter in accordance with embodiments.

FIG. 1 is a block diagram of a medical device 10, which may be used in embodiments. The medical device 10 may have a sensor 12 configured for the collection of a signal representing a physiological parameter. The sensor 12 may be an optical sensor used with a pulse oximeter for the measurement of oxygen saturation in the bloodstream. Furthermore, the sensor 12 may include electrodes for measuring electrical signals from the heart or brain of a patient. The signal from the sensor 12 may be conditioned by an interface 14 prior to being utilized by a microprocessor 16.

In an embodiment, the microprocessor 16 may be connected to random access memory (RAM) 18 and/or read-only memory (ROM) 20. The RAM 18 may be used to store the signals from the sensor 12 and the results of calculations that the microprocessor 16 performs. The ROM 20 may contain code, e.g., machine readable instructions, to direct the microprocessor 16 in collecting and processing the signal. In an embodiment, the microprocessor 16 may be connected to an input device 22 which may be used for local entry of control and calculation parameters for the medical device 10. A display unit 24 may be connected to the microprocessor 16 to display the results the microprocessor 16 has generated from the signal representing the physiological parameter.

In an embodiment, the microprocessor 16 may also be connected to a network interface 26 for the transfer of data from the microprocessor 16 to devices connected to a local area network 28. In an embodiment, the transferred data may include signal data, indices representing the status of physiological conditions, alarm signals, other data, and/or any combination thereof. The transferred data may also consist of control signals from the devices on the local area network 28, for example, to instruct the medical device 10 to send signal data, or other information, to a device on the local area network 28.

In embodiments, the medical device 10 may be used to calculate a reported index with the data collected from the sensor 12, using the method discussed below. The reported index may be output to the display unit 24 or sent to a network device on the local area network 28. The processing may take place in real time, or may be run after the data collection is completed for later determination of an index representing a physiological parameter.

In embodiments, a network device located on the local area network 28 may be used to calculate a reported index with the data collected from the sensor 12, using the method discussed below. The network device may request that the signal be sent from the medical device 10 through the network interface 26. As for the embodiment discussed above, the network device may be used to either determine an index representing a physiological condition in real time or to process a previously collected signal.

In an embodiment, the value of the index representing a physiological condition may be used to trigger one or more alarms, alerting practitioners to clinically important conditions. These alarms may appear on devices on the local area network 28, for example, a patient monitoring screen in an ICU. Alternatively, the alarms may appear on the display unit 24 of the medical device 10. Further, it may be advantageous to activate alarms in both locations using the results from either a local calculation on the medical device 10 or from a remote calculation on a network device connected to the local area network 28.

Embodiments may include a method for the calculation of a smoothed, reported index indicating the status of a medical condition. The method may be used to calculate a reported index indicative of airway instability from blood oxygen saturation data (SpO$_2$). An airway instability index may be used to sound alarms during apnea events or to automatically control treatment systems. The method may utilize information that may occur during each sleep apnea event, called a desaturation pattern or pattern, in which the blood oxygen level falls slowly as oxygen stores in the body are used up, and then sharply recovers as the patient is aroused and hyperventilates. The recurring apnea events may occur in groups of at least two successive patterns, called clusters. In an embodiment, the severity of the apnea may be determined from the number of patterns in each cluster, the time between each pattern, the slope of the drop in the blood oxygen level during a pattern and the slope of the recovery of the blood oxygen level as the patterns ends, and other indications, and/or combinations thereof, among others.

In embodiments, the method may use a number of indices, which may be calculated from the clusters and patterns, to indicate the presence or severity of airway instability, which may be directly related to obstructive sleep apnea, and/or other apneaic events. Embodiments of these indices may include a saturation to ventilation index, an oxygen repletion index, and/or an apnea recovery index, and/or combinations thereof, among others.

In an embodiment, an aggregate index may also be calculated based on the number of breaths, the relative magnitude of the breaths, the slope of the initial 50% of the descending limbs of the desaturations within the cluster and the duration of the clusters, and/or combinations thereof. Embodiments may include an index representing airway instability and may be calculated in a similar manner to those discussed in U.S. Pat. No. 6,760,608 (hereinafter the '608 patent), incorporated by reference as if fully set forth herein. Although the airway instability index may provide a numerical measure of the airway instability and, thus, the presence of apnea, it may have too high of a response to noise or other small changes to be desirable.

In accordance with some embodiments, the airway instability index may include a saturation pattern detection index (SPDi). The SPDi may be defined as a scoring metric associated with the identification of a saturation trend pattern generated in accordance with present embodiment and may correlate to ventilatory instability in a population of sleep lab patients. Specifically, the SPDi may be based on identified clusters of qualified reciprocations in pulse oximetry data. The reciprocations may be identified and qualified using methods and devices as set forth in U.S. Provisional Application No. 61/110,299 filed Oct. 31, 2008, which is incorporated herein by reference in its entirety.

Figure 2:
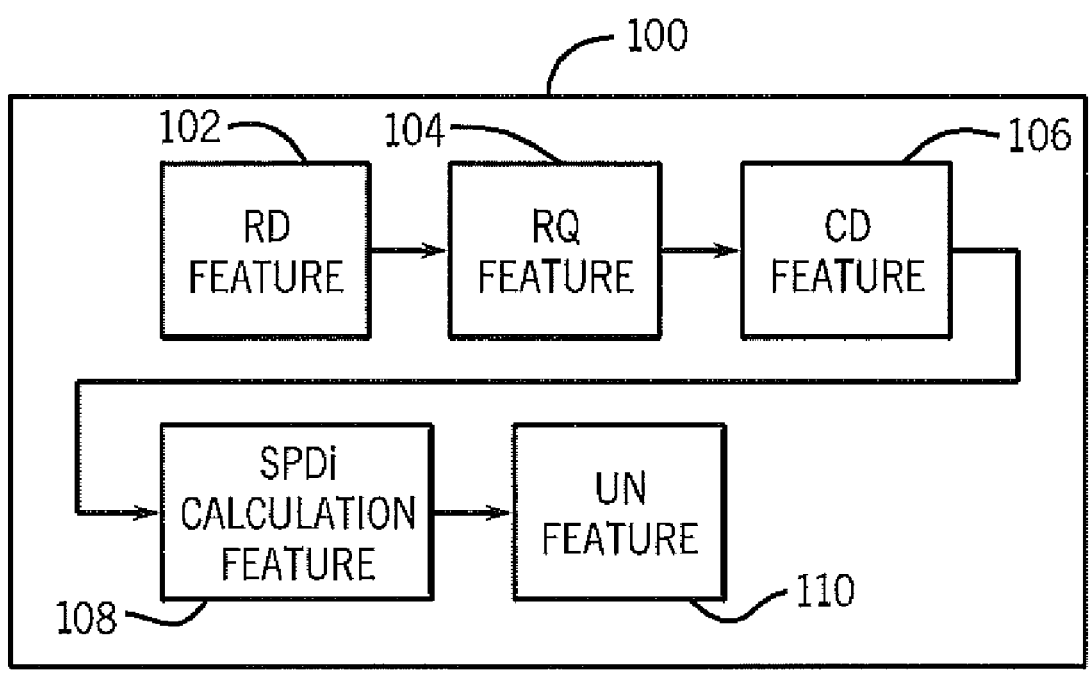
FIG. 2 is a block diagram of an electronic device or pattern detection feature in accordance with present embodiments.

In order to calculate the SPDi, the patterns (i.e., clusters of qualified reciprocations) in $SpO_2$ trend data must first be detected. Accordingly, present embodiments may include code stored on a tangible, computer-readable medium (e.g., a memory) and/or hardware (in the medical device 10 and/or a computer, for instance) capable of detecting the presence of certain patterns in a series of physiologic data. For example, FIG. 2 is a block diagram of an electronic device or pattern detection feature in accordance with present embodiments. The electronic device is generally indicated by the reference number 100 and it may be part of the medical device 10 and/or a separate computer. The electronic device 100 (e.g., an $SpO_2$ monitor and/or memory device) may comprise various subsystems represented as functional blocks in FIG. 2. The various functional blocks shown in FIG. 2 may comprise hardware elements (e.g., circuitry), software elements (e.g., computer code stored on a hard drive or other tangible computer-readable medium) or a combination of both hardware and software elements. For example, each functional block may represent software code and/or hardware components that are configured to perform portions of an algorithm in accordance with present embodiments.

Specifically, in the illustrated embodiment, the electronic device 100 includes a reciprocation detection (RD) feature 102, a reciprocation qualification (RQ) feature 104, a cluster determination (CD) feature 106, a saturation pattern detection index (SPDi) calculation feature 108, and a user notification (UN) feature 110. Each of these components and the coordination of their functions will be summarized and discussed in further detail below. Additional description of these features may be found in U.S. Provisional Application No. 61/110,299 filed Oct. 31, 2008, which is incorporated herein by reference in its entirety.

The RD feature 102 may be capable of performing an algorithm for detecting reciprocations in a data trend. Specifically, the algorithm of the RD feature 102 may perform a statistical method to find potential reciprocation peaks and nadirs in a trend of $SpO_2$ data. A nadir may be defined as a minimum $SpO_2$ value in a reciprocation. The peaks may include a rise peak (e.g., a maximum $SpO_2$ value in a reciprocation that occurs after the nadir) and/or a fall peak (e.g., a maximum $SpO_2$ value in a reciprocation that occurs before the nadir).

In one embodiment, a window size for calculations related to identifying peaks and nadirs may be set based on historical values (e.g., average duration of a set number of previous reciprocations). For example, in one embodiment, a window size may be set to the average duration of all qualified reciprocations in a certain time period (e.g., the last 6 minutes) divided by 2. In another embodiment, a dynamic window method may be utilized wherein the window size may be initially set to a certain amount of time (e.g., 12 seconds) and then increased as the length of qualified reciprocations increases. This may be done in anticipation of larger reciprocations because reciprocations that occur next to each other tend to be of similar shape and size. If the window remained at the initial time setting (e.g., 12 seconds), it could potentially be too short for larger reciprocations and may prematurely detect peaks and nadirs. The following equation or calculation is representative of a window size determination, wherein the output of the filter is inclusively limited to 12-36 seconds, and the equation is executed each time a new reciprocation is qualified:

If no qualified reciprocations in the last 6 minutes:
Window Size=12 (initial value)
else:

RecipDur=½*current qualified recip duration+ ½*previous RecipDur

Window Size=bound(RecipDur,12,36).

With regard to $SpO_2$ signals that are essentially flat, the dynamic window method may fail to find the three points (i.e., a fall peak, a rise peak, and a nadir) utilized to identify a potential reciprocation. Therefore, the RD feature 102 may limit the amount of time that the dynamic window method can search for a potential reciprocation. For example, if no reciprocations are found in 240 seconds plus the current dynamic window size, the algorithm of the RD feature 102 may timeout and begin to look for potential reciprocations at the current $SpO_2$ trend point and later. The net effect of this may be that the RD feature 102 detects potential reciprocations less than 240 seconds long.

Once potential peaks and nadirs are found using the RD feature 102, the RQ feature 104 may pass the potential reciprocations through one or more qualification stages to determine if a related event is caused by ventilatory instability. A first qualification stage may include checking reciprocation metrics against a set of limits (e.g., predetermined hard limits). A second qualification stage may include a linear qualification function. In accordance with present embodiments, a potential reciprocation may be required to pass through both stages in order to be qualified. Details regarding these qualification stages may be found in U.S. Provisional Application No. 61/110,299 filed Oct. 31, 2008, which is incorporated herein by reference in its entirety.

As an example, in a first qualification stage, which may include a limit-based qualification, four metrics may be calculated for each potential reciprocation and compared to a set of limits. Any reciprocation with a metric that falls outside of these limits may be disqualified. The limits may be based on empirical data. For example, in some embodiments, the limits may be selected by calculating the metrics for potential reciprocations from sleep lab data where ventilatory instability is known to be present, and then comparing the results to metrics from motion and breathe-down studies. The limits may then be refined to filter out true positives.

A second qualification stage of the RQ feature 104 may utilize a object reciprocation qualification feature. Specifically, the second qualification stage may utilize a linear qualification function based on ease of implementation, efficiency, and ease of optimization. The equation may be determined by performing a least squares analysis. For example, such an analysis may be performed with MATLAB®. The inputs to the equation may include the set of metrics disclosed in U.S. Provisional Application No. 61/110,299 filed Oct. 31, 2008. The output may be optimized to a maximum value for patterns where ventilatory instability is known to be present. The equation may be optimized to output smaller values (e.g., 0) for other data sets where potential false positive reciprocations are abundant.

The CD feature 106 may be capable of performing an algorithm that maintains an internal reciprocation counter that keeps track of a number of qualified reciprocations that are currently present. When the reciprocation counter is greater than or equal to a certain value, such as 5, the clustering state may be set to "active" and the algorithm may begin calculating and reporting the SPDi. When clustering is not active (e.g., reciprocation count<5) the algorithm may not calculate the SPDi. Once clustering is active, it may remain active until the time between two qualified reciprocations exceeds a certain time value, such as 120 seconds.

When the clustering state is active, the SPDi calculation feature 108 may calculate an unfiltered SPDi for each new qualified reciprocation. The following formula is an example of a formula that may be used by the SPDi calculation feature 108:

$$\text{Unfiltered SPDi} = a*\text{Magnitude} + b*\text{PeakDelta} + c*\text{NadirDelta};$$

wherein $a=1.4$, $b=2.0$, $c=0.2$;

wherein Magnitude=average magnitude of all reciprocations in the last 6 minutes;

wherein PeakDelta=average of the three highest qualified reciprocation rise peaks in the last 6 minutes minus the average of the three lowest qualified reciprocation rise peaks in the last 6 minutes; and wherein NadirDelta=average of the three highest qualified reciprocation nadirs in the last 6 minutes minus the average of the three lowest qualified reciprocation nadirs in the last 6 minutes.

The above formula may be utilized to quantify the severity of a ventilatory instability pattern. The constants and metrics used may be based on input from clinical team members. It should be noted that the PeakDelta parameter may be assigned the largest weighting constant since the most severe patterns generally have peak reciprocation values that do not recover to the same baseline.

The unfiltered SPDi may be updated whenever clustering is active and a new qualified reciprocation is detected. Non-zero SPDi values may be latched for a period of time (e.g., 6 minutes). The unfiltered SPDi may then be low pass filtered to produce the final output SPDi value. The following infinite impulse response (IIR) filter with a response time of approximately 40 seconds is an example of what may be used:

$$SPDi = \text{Unfiltered } SPDi/a + \text{Previous Filtered } SPDi*(a-1)/a;$$

wherein $a=40$.

Figure 3:
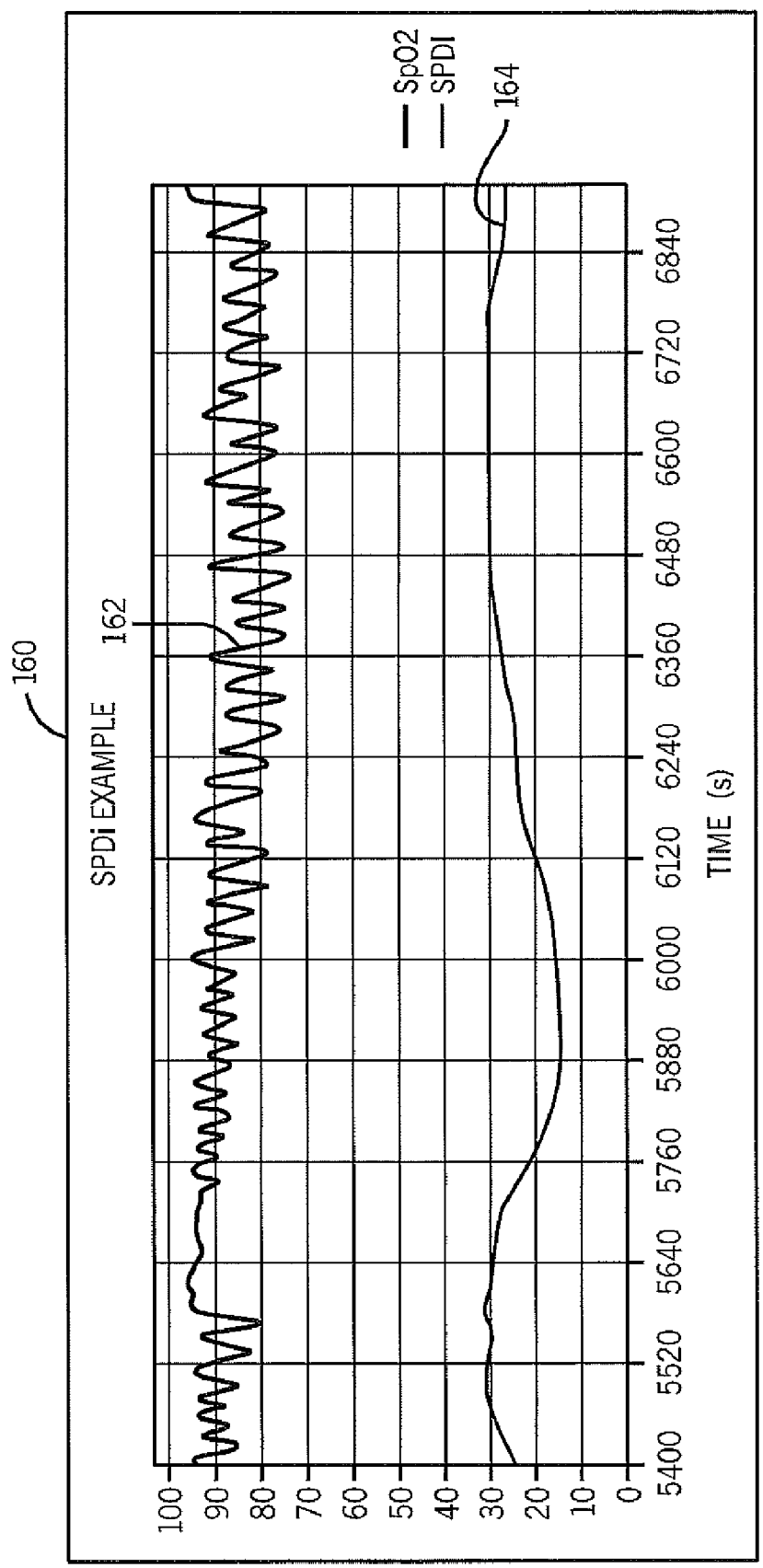
FIG. 3 is an exemplary graph including an SpO$_2$ trend that contains a ventilatory instability SpO$_2$ pattern and a trend of the resulting SPDi in accordance with embodiments.

FIG. 3 is an exemplary graph 160 including an $SpO_2$ trend 162 that contains a ventilatory instability $SpO_2$ pattern and a trend of the resulting SPDi 164. In the illustrated example, it should be noted that the SPDi is sensitive to the decreasing peaks (incomplete recoveries) starting at approximately $t=6000$.

The UN feature 110 may be capable of determining if a user notification function should be employed to notify a user (e.g., via a graphical or audible indicator) of the presence of a detected patterns such as ventilatory instability. The determination of the UN feature 110 may be based on a user configurable tolerance setting and the current value of the SPDi. For example, the user may have four choices for the sensitivity or tolerance setting: Off, Low, Medium, and High. When the sensitivity or tolerance setting is set to Off, an alarm based on detection of a saturation pattern may never be reported to the user. The other three tolerance settings (i.e., Low, Medium, and High) may each map to an SPDi threshold value. For example, Low may map to an SPDi threshold of 6, Medium may map to an SPDi threshold of 15, and High may map to an SPDi threshold of 24. The thresholds may be based on input from users. When the SPDi is at or above the threshold for a given tolerance setting, the user may be notified that ventilatory instability is present.

Figure 4:
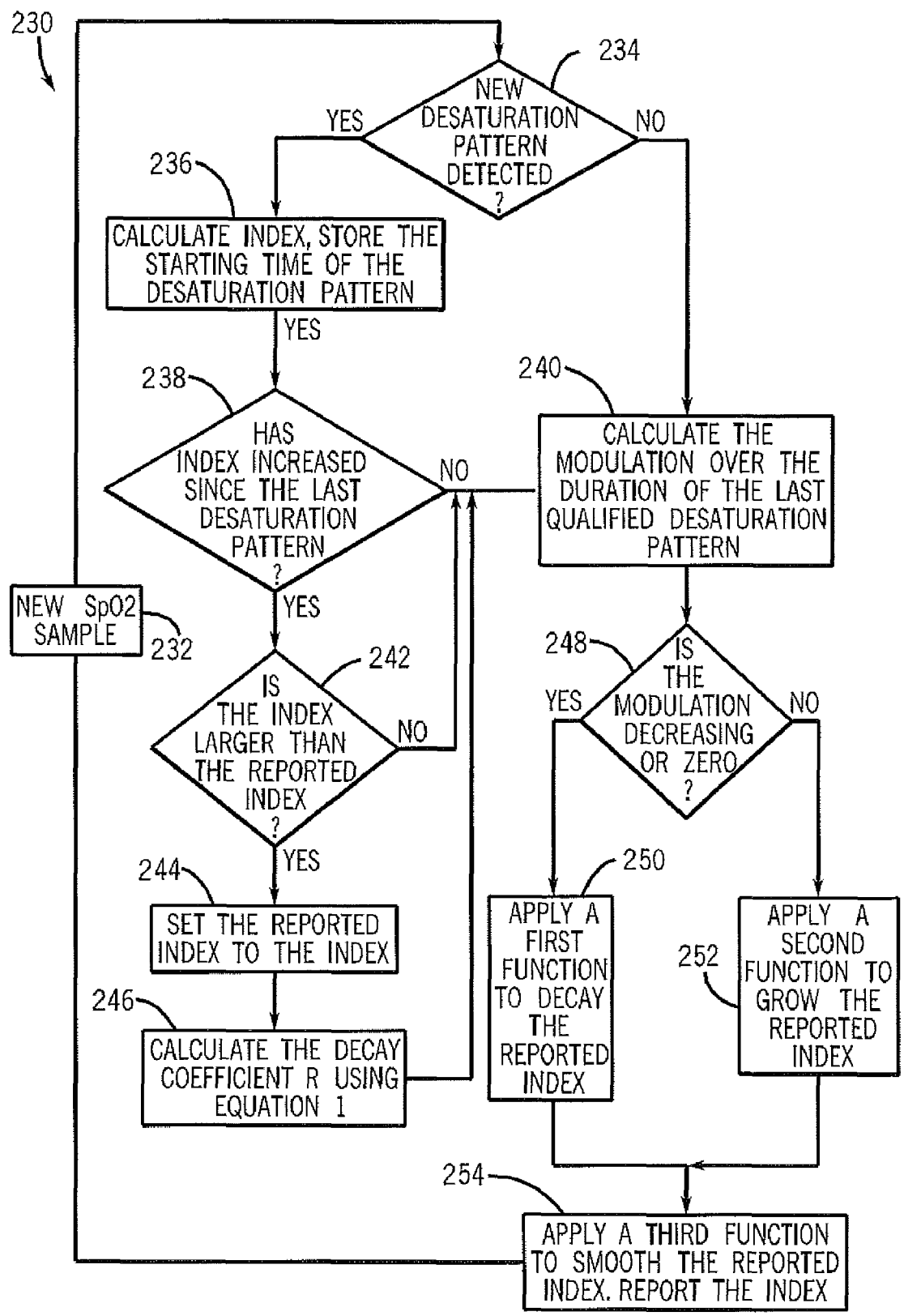
FIG. 4 is a process flow diagram showing a method for minimization of noise in the calculation of an airway instability index in accordance with embodiments.

FIG. 4 is a process flow diagram showing an embodiment of a method 230 capable of the minimization of noise in the calculation of an airway instability index. The method 230 may begin with the collection of a new sample of the percent saturation of oxygen in the bloodstream, or $SpO_2$, as shown in block 232. Over time, these samples provide a signal representing the $SpO_2$ level. After the collection of each new $SpO_2$ sample, the signal may be analyzed to determine if a new, or qualified, pattern has been detected, as shown in block 234. In an embodiment, this determination may be performed by any number of different techniques. One of ordinary skill in the art will appreciate that other methods may be used for the determination of the presence of qualified patterns and/or other patterns.

In an embodiment, if a qualified pattern is detected, the starting time of the qualified pattern may be reported and a new airway instability index may be calculated, as shown in block 236. The airway instability index may be calculated, for example, by using the method set forth above, the method disclosed in the '608 patent, or the method disclosed in U.S. Provisional Application No. 61/110,299 filed Oct. 31, 2008. One of ordinary skill in the art will appreciate that other methods may be used for calculation of an effective airway instability index.

In an embodiment, as shown in block 238, the new value for the airway instability index may be compared to the last value of the airway instability index, and if it is less than or equal to that value, the method 230 may proceed with the acts starting at block 240, as discussed below. The new value for the airway instability index may then be compared to the current value of the reported index, as shown in block 242, and if it is less then or equal to the current value of the reported index, the method 230 may proceed with the acts starting at block 240.

In an embodiment, if the new value for the airway instability index is greater than the current value of the reported index, the reported index may be set to the new value of the airway instability index, as shown in block 244. A decay coefficient may be then calculated for use in the remaining acts, as shown in block 246. In an embodiment, the decay coefficient may be calculated by the formula of the general form shown in equation 1:

$$R = T^2/(\text{Airway Instability Index}), \quad \text{(equation 1)}$$

where T is the desired decay period. In an embodiment, T is 180 seconds. Those skilled in the art will recognize that other values may be used for T, and in fact, T may be tuned to give optimum values needed for the particular application and index selected.

In an embodiment, if no new pattern is detected, and/or upon completion of the acts discussed above, in block 240, a value may be calculated for the percent modulation of the SpO$_2$ trend over the duration of the current qualified pattern. In an embodiment, a fixed or variable length sliding window could also be for the percent modulation and mean calculations. In an embodiment, this calculation may be performed using the formula of the general form shown in equation 2:

$$\text{Percent Modulation} = (SpO_2^{max} - SpO_2^{min})/SpO_2^{mean}. \quad \text{(equation 2)}$$

As shown in block 248, the calculated value for the percent modulation may be compared to the previous value of the percent modulation. If the percent modulation has decreased or is unchanged from the last value, the reported index may be decreased, as shown in block 250. In an embodiment, this decrease in the reported index may be performed by using the parabolic decay function of the general form shown in equation 3:

$$\text{New Reported Index} = \text{Previous Preported Index} - (2N/R), \quad \text{(equation 3)}$$

where N is the duration of the current qualified pattern in seconds, calculated from the starting time recorded in block 236, and R is the decay coefficient calculated in equation 1. If the value calculated for the reported index is less than zero, the reported index may be set to zero. One of ordinary skill in the art will recognize that other functions may be selected for decreasing the value of the new unfiltered index. Such functions may include exponential decay functions, quadratic functions, and/or other functions appropriate for the application and index selected. The choice of the function may depend on, for example, the noise of the unfiltered index, the sensitivity desired, and/or the desired response to sudden changes in the index. In an embodiment, an exponential decay function may be desired if a faster response to changes is desirable.

In an embodiment, if the value for percent modulation has increased, the instability index may be increased, as shown in block 252. In an embodiment, this calculation may be performed using a parabolic growth function of the general form shown in equation 4:

$$\text{New Reported Index} = \text{Previous Reported Index} + (2N/R), \quad \text{(equation 4)}$$

where N is the duration of the current qualified pattern in seconds, calculated from the starting time recorded in block 236, and R is the decay coefficient calculated in block 246. If the value calculated for the reported index is greater then a maximum value for the airway instability index selected, then the reported index may be set to the maximum value. One skilled in the art will recognize that other functions may be selected for increasing the value of the reported index. Such functions may include exponential growth functions, quadratic functions, or other functions appropriate for the application and index selected. The selection of an appropriate function will depend on the responsiveness desired, as the function will control how fast the reported index increases or decreases.

In an embodiment, the reported index may be subjected to a filtering step prior to reporting the value of the index, as shown in block 254. In an embodiment, this filtering step may be performed by an infinite impulse response (IIR) filter, of the general form shown in equation 5:

$$\text{Reported Index} = \text{New Reported Index}/W + \text{Previous Reported Index} \ast ((W-1)/W), \quad \text{(equation 5)}$$

where W is the IIR filter weight. In an embodiment, a weight of four is used. One skilled in the art will recognize that other weights, or even other functions, may be selected for filtering the value of the new unfiltered index. Alternate weights may be selected to optimize performance of the filter for the index selected. Examples of other filtering functions that may be used include functions such as mean filters, median filters, Gaussian smoothing functions, Savitzky-Golay filters, and/or other functions appropriate for the application and index selected. The choice of the filtering function depends on factors such as the sensitivity desired and the amount of tolerable fluctuation, or noise, in the index, among others.

FIGS. 5-8 are graphs showing the output from embodiments of methods such as, but not limited to, method 230 discussed above. In each of these charts, the left hand vertical axis 256 represents the value of the oxygen saturation, or SpO$_2$, in the blood of a patient. The horizontal axis 258 represents the time, in seconds, of a data collection sequence. Accordingly, the SpO$_2$ signal 260 from a pulse oximeter output may be plotted against these axes 256, 258 to show the change in the blood oxygen level of a patient over time.

The SpO$_2$ signal 260 may be used to calculate an airway instability index 262, which may be useful in determining if a patient is having an episode of obstructive sleep apnea and/or other event. The airway instability index 262 may also be used by the method 230 discussed with respect to FIG. 4 to create a reported index 264, which may have less noise than the airway instability index 262 and, thus, may be more valuable to a practitioner. In the charts of FIGS. 5-8, both the airway instability index 262 and the reported index 264 are plotted against the right hand axis 266, which represents a relative measure for the two indices 262, 264. One of ordinary skill in the art will recognize that similar results will be obtained from the method 230 as applied to indices measuring other physiological parameters.

The line 268, drawn across the chart at the 85% level for SpO$_2$, may indicate a level that may generally be considered important by practitioners. This level may be used as a setpoint in embodiments.

Figure 5:
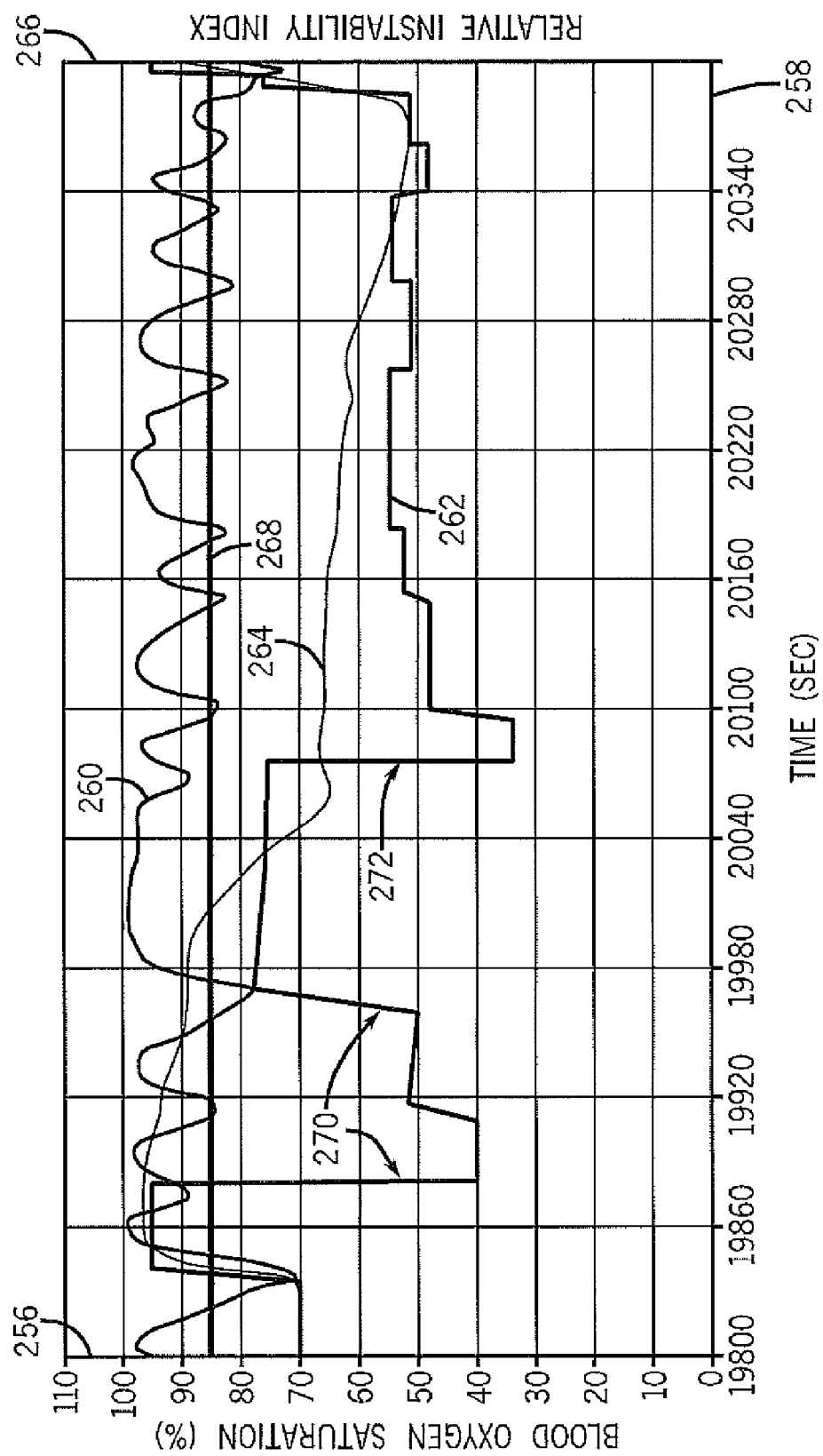
FIG. 5 is a graphical representation of SpO$_2$ data which may be useful to explain the operation of embodiments with respect to short term decreases in an index.

FIG. 5 is a graph showing SpO$_2$ data which may be useful to demonstrate the stability of an embodiment when very short term decreases occur in an index. In an embodiment, the relatively high variability and rapid changes that may occur in an airway instability index 262 may be exemplified by the sudden drop at around 19870 seconds followed by a sudden rise at around 19970 seconds, as indicated by reference number 270. The magnitude and short time span of these changes may be dismissed by a practitioner as happening over too short of a time scale to be a physiologically significant indicator of patient condition or of recovery from a previous pattern.

In contrast, the reported index 264, generated by the method 230 discussed with respect to FIG. 4 shows a relatively small continuing decrease throughout those time periods. Because the reported index 264 is higher than the rapidly changing airway instability index 262, the clinician may already be on alert that issues may be present. In another example, with regard to FIG. 4, the precipitous drop at around 20070 seconds, indicated by reference numeral 272, may be interpreted as an oversensitivity of the airway instability index 262, rather than a meaningful indicator of patient condition or recovery. In contrast to this, the reported index 264 from a method shows a gradual decrease during this period.

Figure 6:
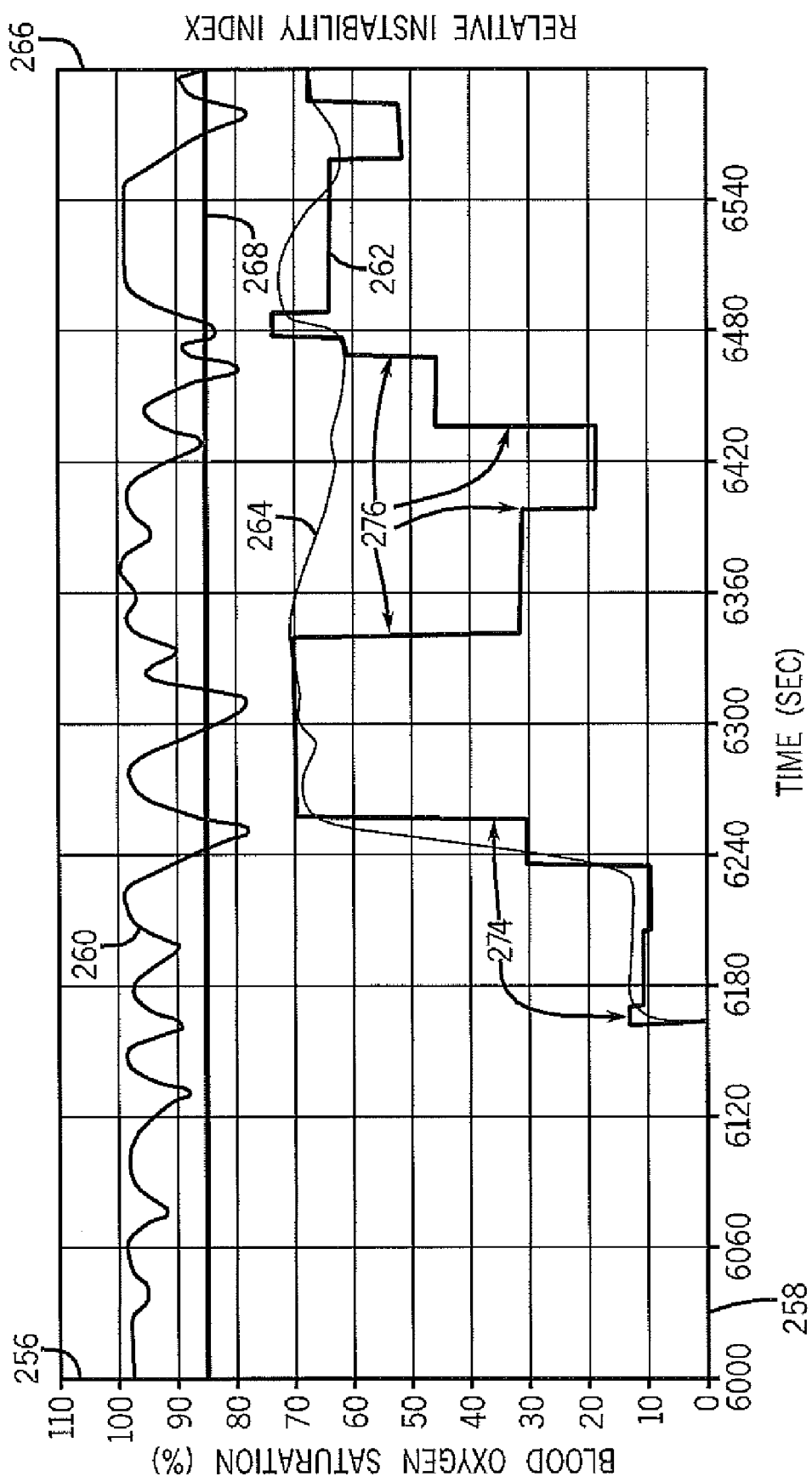
FIG. 6 is a graphical representation of SpO$_2$ data which may be useful to explain the operation of embodiments with respect to significant increases in an index.

A practitioner may be more likely to be concerned with significant shifts upward in the airway instability index 262, than with the downward shifts discussed above. As shown in blocks 242 and 244 of the flowchart in FIG. 4, when the airway instability index 262 is greater than the reported index 264, the reported index 264 may be set to the value of the airway instability index 262. The results of this are illustrated in the chart of FIG. 6, which is useful to demonstrate the response of an embodiment to sudden increases in an index. Precipitous rises in the airway instability index 262, as seen around 6160 and 6250 seconds (indicated by reference numeral 274), may result in corresponding increases in the reported index 264, ensuring that the clinician is warned when significant increases occur.

In an embodiment, the stability of the method 230 to fast changes in the airway instability index 262, e.g., noise, is also demonstrated in FIG. 6. For example, the precipitous downward shifts in the airway instability index 262 at around 6340 and 6400 seconds followed by upward shifts at around 6430 and 6470 seconds (indicated by reference numeral 276) do not cause a significant change in the reported index 264, as the reported index 264 is already at a higher value than the airway instability index 262.

Figure 7:
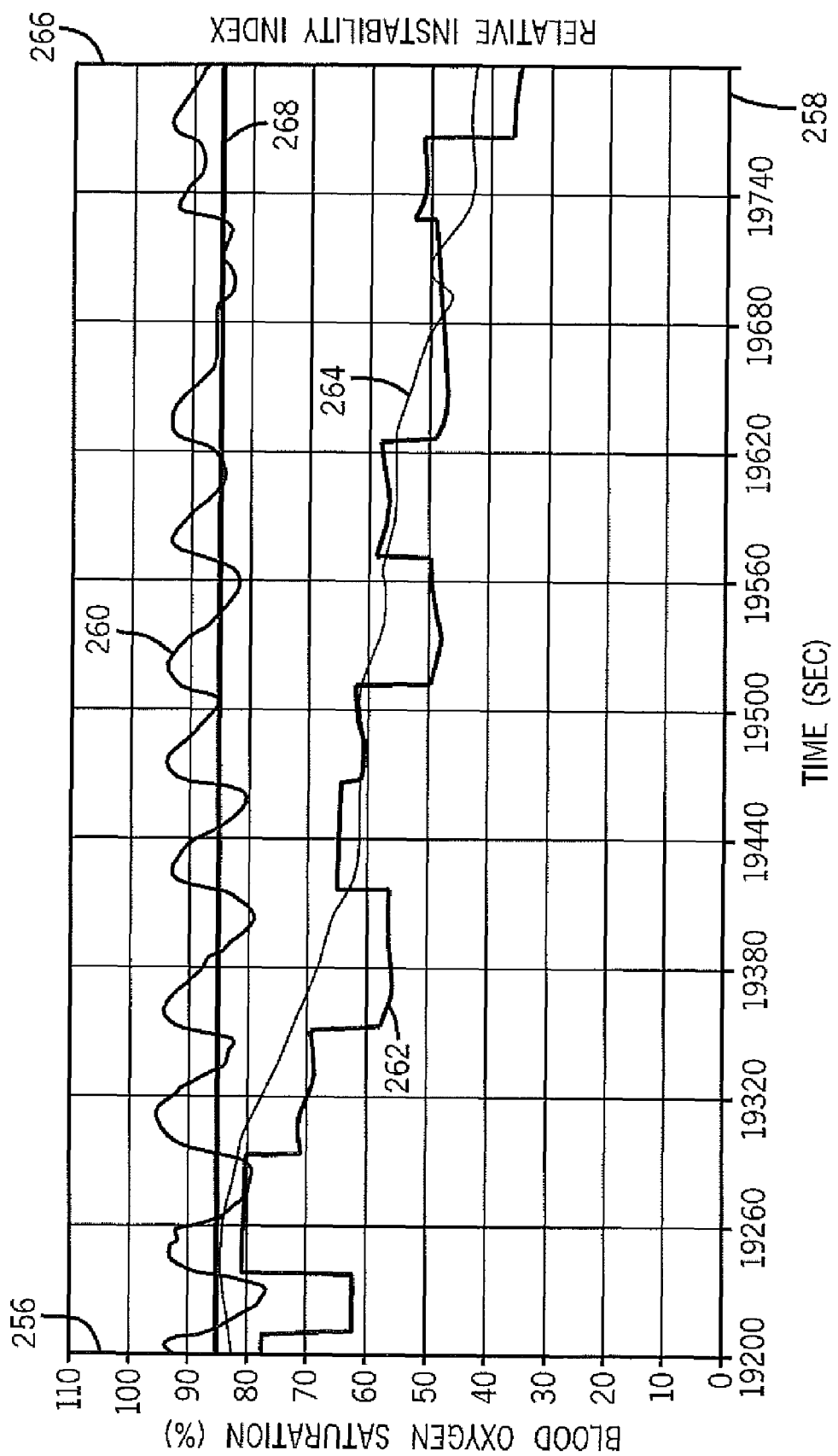
FIG. 7 is a graphical representation of SpO$_2$ data which may be useful to explain the operation of embodiments with respect to lowered noise response.

In an embodiment, the decreased response to noise provided by the method 230 is further illustrated by the chart in FIG. 7. In FIG. 7, the airway instability index 262 is falling over time, but shows numerous deviations up and down that may tend to obscure this trend. In contrast, the reported index 264 shows a relatively smooth decrease over the same time period, highlighting the trend.

Figure 8:
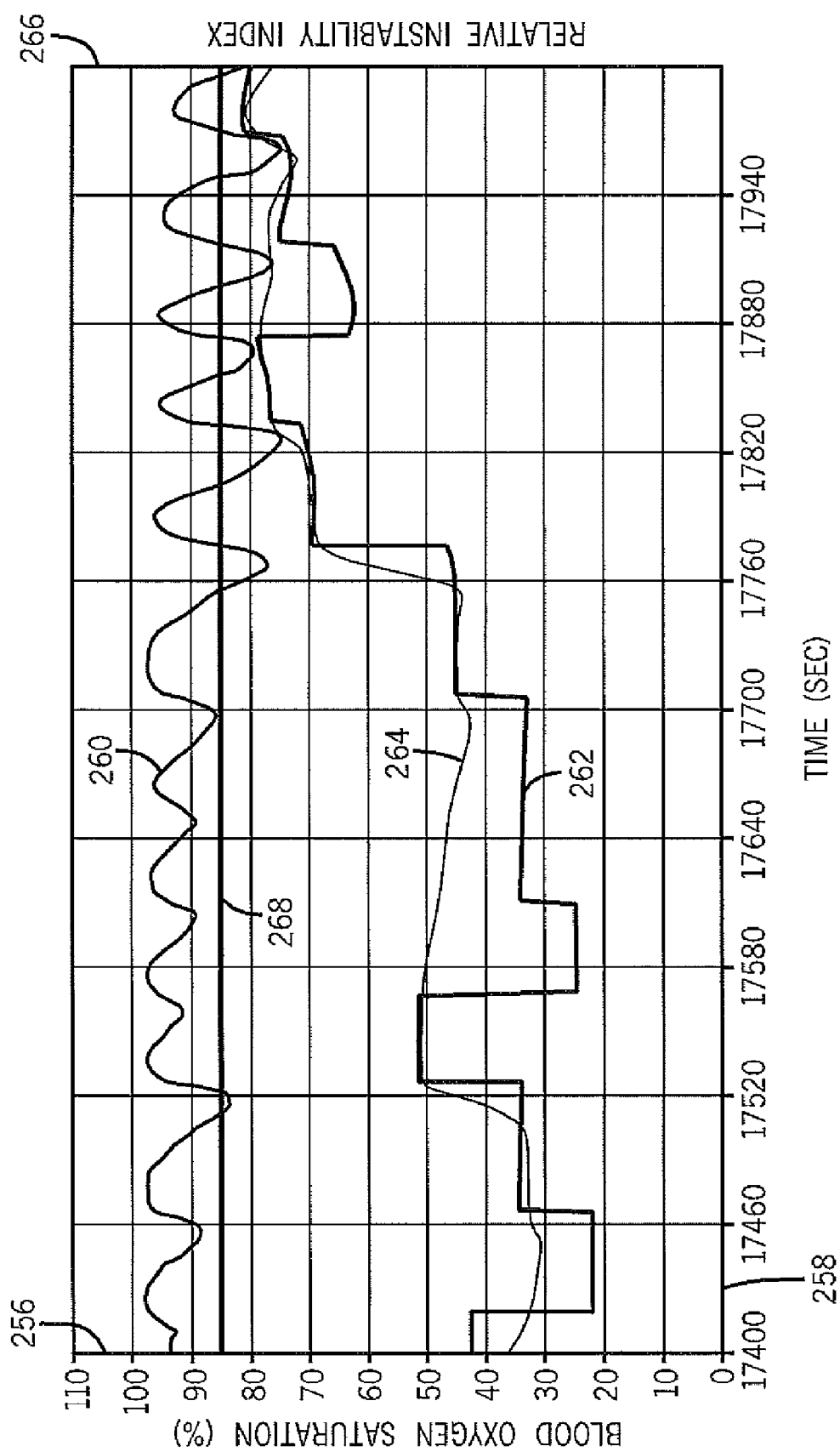
FIG. 8 is a graphical representation of SpO$_2$ data which may be useful to explain the operation of an embodiment of the present invention with respect to significant decreases in SpO$_2$.

FIG. 8 is chart of $SpO_2$ data which may be useful to demonstrate the operation of an embodiment as the patient enters a clinically significant period. In FIG. 8, both the stability and responsiveness of the current method are demonstrated. While the airway instability index 262 shows a number of decreases and increases, only a few of the changes are likely to be significant to a practitioner. The reported index 264 immediately follows any upward shift in the airway instability index 262 that is greater then the current value of the reported index 264 while ignoring sudden decreases that are already below the current value of the reported index 264. Thus, the reported index 264 may only show fast changes at clinically significant points.

While the present disclosure described above may be susceptible to various modifications and alternative forms, specific embodiments have been shown by way of example in the drawings and have been described in detail herein. However, it should be understood that the present disclosure is not intended to be limited to calculating an airway instability index. Indeed, the present disclosure may not only be applied to airway instability indices, but may also be utilized for the reporting of other physiological parameters needing a high response to significant events with low noise. The present disclosure is intended to cover all modifications, equivalents, and alternatives falling within the spirit and scope of the present disclosure as defined by the following appended claims.

What is claimed is:

1. A method of evaluating physiological parameter data, comprising:
   monitoring a patient to produce a signal comprising a sequence of numerical values for a physiological parameter over a time period;
   calculating an index based at least in part upon the signal;
   comparing the calculated index to a reported index, and if the calculated index is greater than the reported index, setting the reported index to the value of the calculated index;
   calculating a modulation of the signal, wherein the modulation comprises the difference between a maximum value of the signal and a minimum value of the signal divided by a mean value of the signal over a period of time;
   comparing the modulation to a previous value of the modulation of the signal to identify a trend in the modulation, and if the trend corresponds to an undesirable condition, using a first function capable of increasing the reported index; and
   providing an indication of a physiological status based at least in part upon the reported index.

2. The method of claim 1, wherein the index comprises an airway instability index.

3. The method of claim 1, wherein the period of time comprises a period of time over which a qualified pattern is occurring.

4. A method of evaluating physiological parameter data, comprising:
   monitoring a patient to produce a signal comprising a sequence of numerical values for a physiological parameter over a time period;
   calculating an index based at least in part upon the signal;
   comparing the calculated index to a reported index, and if the calculated index is greater than the reported index, setting the reported index to the value of the calculated index;
   calculating a modulation of the signal;
   comparing the modulation to a previous value of the modulation of the signal to identify a trend in the modulation, and if the trend corresponds to an undesirable condition, using a first function capable of increasing the reported index, wherein the first function comprises a parabolic growth function, and/or an exponential growth function; and
   providing an indication of a physiological status based at least in part upon the reported index.

5. The method of claim 4, comprising applying a second function capable of decreasing the reported index, if the trend does not correspond to an unfavorable condition.

6. A method of evaluating physiological parameter data, comprising:
   monitoring a patient to produce a signal comprising a sequence of numerical values for a physiological parameter over a time period;
   calculating an index based at least in part upon the signal;
   comparing the calculated index to a reported index, and if the calculated index is greater than the reported index, setting the reported index to the value of the calculated index;
   calculating a modulation of the signal,
   comparing the modulation to a previous value of the modulation of the signal to identify a trend in the modulation, and if the trend corresponds to an undesirable condition, using a first function capable of increasing the reported index;
   applying a second function capable of decreasing the reported index, if the trend does not correspond to an unfavorable condition;
   filtering the reported index by a third function, wherein the third function comprises an infinite impulse response filter; and
   providing an indication of a physiological status based at least in part upon the reported index.

7. A medical device, comprising:
   a microprocessor configured to process a signal associated with at least one physiological parameter of a patient; and a memory configured to store machine readable instructions which, if executed, are capable of causing the microprocessor to:

calculate an index from the signal;

compare the calculated index to a reported index, and if the calculated index is greater than the reported index, set the reported index to the value of the calculated index;

calculate a modulation of the numerical signal, wherein the modulation comprises the difference between a maximum value of the numerical signal and a minimum value of the numerical signal divided by a mean value of the numerical signal over a period of time;

compare the modulation to a previous value of the modulation to identify a trend in the modulation, and if the trend corresponds to an undesirable condition, increase the reported index using a first function; and provide an indication of a physiological status based on the reported index.

8. The medical device of claim 7, wherein the contents of the memory comprises machine readable instructions which, if executed, are capable of causing the microprocessor to apply a second function to decrease the reported index, if the trend does not correspond to an unfavorable condition.

9. The medical device of claim 8, wherein the machine readable instructions, if executed, are capable of causing the microprocessor to filter the reported index by a third function.

10. The medical device of claim 7, comprising a network interface unit capable of sending information comprising the numerical signal, and/or the reported index, to a device located on a local area network.

11. The medical device of claim 7, wherein the index comprises an airway instability index.

12. A medical device, comprising:
a microprocessor configured to process a signal associated with at least one physiological parameter of a patient; and
a memory configured to store machine readable instructions which, if executed, are capable of causing the microprocessor to:
calculate an index from the signal;
compare the calculated index to a reported index, and if the calculated index is greater than the reported index, set the reported index to the value of the calculated index;
calculate a modulation of the numerical signal;
compare the modulation to a previous value of the modulation to identify a trend in the modulation, and if the trend corresponds to an undesirable condition, increase the reported index using a first function, wherein the first function comprises a parabolic growth function, and/or an exponential growth function; and
provide an indication of a physiological status based on the reported index.

13. A medical device, comprising:
a microprocessor configured to process a signal associated with at least one physiological parameter of a patient; and
a memory configured to store machine readable instructions which, if executed, are capable of causing the microprocessor to:
calculate an index from the signal;
compare the calculated index to a reported index, and if the calculated index is greater than the reported index, set the reported index to the value of the calculated index;
calculate a modulation of the numerical signal;
compare the modulation to a previous value of the modulation to identify a trend in the modulation, and if the trend corresponds to an undesirable condition, increase the reported index using a first function;
apply a second function to decrease the reported index, if the trend does not correspond to an unfavorable condition;
filter the reported index by a third function, wherein the third function comprises an infinite impulse response filter; and
provide an indication of a physiological status based on the reported index.

14. A method of evaluating physiological parameter data, comprising:
monitoring a patient to produce a signal comprising a sequence of numerical values for a physiological parameter over a time period;
detecting potential reciprocations by detecting potential reciprocation peaks and nadirs in the sequence of numerical values;
determining whether the potential reciprocations are qualified by comparing metrics of the potential reciprocations with a set of limits and performing a linear qualification function;
tracking a number of qualified reciprocations identified within a window of time and calculating an index when the number of qualified reciprocations identified within the window of time reaches or surpasses a limit;
comparing the calculated index to a reported index, and if the calculated index is greater than the reported index, setting the reported index to the value of the calculated index; and
providing an indication of a physiological status based at least in part upon the reported index.

15. The method of claim 14, comprising:
calculating a modulation of the signal; and
comparing the modulation to a previous value of the modulation to identify a trend in the modulation and if the trend corresponds to an undesirable condition, using a first function capable of increasing the reported index.

16. The method of claim 14, comprising calculating the index based at least in part upon an average magnitude of all qualified reciprocations within a time period relative to the current time, an average of a fixed number of the highest reciprocation peaks of qualified reciprocations within the time period, and/or an average of a fixed number of the highest reciprocation nadirs of qualified reciprocations within the time period, and/or combinations thereof.

17. The method of claim 14, wherein the window of time may be defined based on historical values.

* * * * *